US005981263A

United States Patent [19]
Hillman et al.

[11] Patent Number: 5,981,263
[45] Date of Patent: Nov. 9, 1999

[54] HUMAN MATRILIN-3

[75] Inventors: Jennifer L. Hillman, Mountain View; Preeti Lal, Sunnyvale; Neil C. Corley, Mountain View; Purvi Shah, Sunnyvale; Matthew Kaser, Castro Valley, all of Calif.

[73] Assignee: Incyte Pharmaceuticals, Inc., Palo Alto, Calif.

[21] Appl. No.: 08/897,443

[22] Filed: Jul. 21, 1997

[51] Int. Cl.$^6$ .......................... C07H 21/04; C12N 15/11; C12N 15/63; C12N 1/21

[52] U.S. Cl. ..................... 435/252.3; 536/24.31; 536/23.5; 435/69.1; 435/320.1; 435/325; 435/254.2

[58] Field of Search ................. 536/23.5, 24.31; 435/69.1, 320.1, 252.3, 325, 254.2

[56] References Cited

PUBLICATIONS

New England Biolabs catalog, 1993/94.
Accession No. N26805 Dec. 29, 1995 Genebank.
Accession No. A27272 Oct. 11, 1995 Genebank.
Accession No. AA121267 May 14, 1997 Genebank.
Accession No. W67469 Oct. 16, 1996 Genbank.
Accession No. AA121420 May 14, 1997 Genbank.
Accession No. AA167466 Dec. 19, 1996 Genbank.
McGowan, S.E., "Extracellular matrix and the regulation of lung development and repair", *FASEB J*, 6:2895–2904 (1992).
Grant, D.S., et al., "Regulation of capillary formation by laminin and other components of the extracellular matrix", *EXS*, 79:317–333 (1997).
Taipale, J., et al., "Growth factors in the extracellular matrix", *FASEB J* 11:51–59 (1997).
Eleftheriou, C.S., et al., "Cellular ageing related proteins secreted by human fibroblasts", *Mutation Research*, 256:127–138 (1991).
Engel, J., et al., "Domain organizations of extracellular matrix proteins and their evolution", *Development Supplement*, 35–42 (1994).
Deak, F., et al., "Primary Structure and Expression of Matrilin–2, the Closest Relative of Cartilage Matrix Protein Within the von Willebrand Factor Type A–like Module Superfamily", *J Biol Chem*, 272:9268–9274 (1997). (GI 2072792).

Jenkins, R.N., et al., "Structure and Chromosomal Location of the Human Gene Encoding Cartilage Matrix Protein", *J Biol Chem*, 265:19624–19631 (1990). (GI 1732121).

Aszodi, A., et al., "Cloning, sequencing and expression analysis of mouse cartilage matrix protein cDNA", *Eur J Biochem*, 236:970–977 (1996).

Colombatti, A., et al., "The Superfamily of Proteins With von Willebrand Factor Type A–like Domains: One Theme Common to Components of Extracellular Matrix, Hemostasis, Cellular Adhesion, and Defense Mechanisms", *Blood*, 77:2305–2315 (1991).

Lee, J.O., et al., "Crystal Structure of the A Domain from the α Subunit of Integrin CR3 (CD11b/CD18)", *Cell*, 80:631–638 (1995).

Saxne, T., et al., "Cartilage Oligomeric Matrix Protein: A Novel Marker of Cartilage Turnover Detectable in Synovial Fluid and Blood", *British Journal of Rheumatology*, 31:583–591 (1992).

Malemud, C.J., "Markers of osteoarthritis and cartilage research in animal models", *Curr Opin Rheumatol*, 5:494–502 (1993).

Loughlin, J., et al., "Exclusion of the cartilage link protein and the cartilage matrix protein genes as the mutant loci in several heritable chondrodysplasia", *Hum Genet*, 94:698–700 (1994).

Hecht, J.T., et al., "Mutations in exon 17b of cartilage oligometric matrix protein (COMP) cause pseudoachondroplasia", *Nat Genet*, 10:325–329 (1995).

Paulsson, M., et al., "Radioimmunoassay of the 148–kilodalton cartilage protein", *Biochem. J.*, 207:207–213 (1982).

*Primary Examiner*—Nancy A Johnson
*Attorney, Agent, or Firm*—Incyte Pharmaceuticals, Inc.

[57] ABSTRACT

The invention provides a human matrilin-3 (MAT-3) and polynucleotides which identify and encode MAT-3. The invention also provides expression vectors, host cells, agonists, antibodies and antagonists. The invention also provides methods for treating disorders associated with expression of MAT-3.

8 Claims, 18 Drawing Sheets

```
5' GGT AGC CGA CGC GCC GGC CGG CGC GTG ACC TTG CCC CTC TTG CTC GCC TTG AAA
      9          18          27          36          45          54

ATG GAA AAG ATG CTC GCA GGC TGC TTT CTG CTG ATC CTC GGA CAG ATC GTC CTC
M   E   K   M   L   A   G   C   F   L   L   I   L   G   Q   I   V   L
      63          72          81          90          99         108

CTC CCT GCC GAG GCC AGG GAG CGG TCA CGT GGG AGG TCC ATC TCT AGG GGC AGA
L   P   A   E   A   R   E   R   S   R   G   R   S   I   S   R   G   R
     117         126         135         144         153         162

CAC GCT CGG ACC CAC CCG CAG ACG GCC CTT CTG GAG AGT TCC TGT GAG AAC AAG
H   A   R   T   H   P   Q   T   A   L   L   E   S   S   C   E   N   K
     171         180         189         198         207         216

CGG GCA GAC CTG GTT TTC ATC ATT GAC AGC TCT CGC AGT GTC AAC ACC CAT GAC
R   A   D   L   V   F   I   I   D   S   S   R   S   V   N   T   H   D
     225         234         243         252         261         270

TAT GCA AAG GTC AAG GAG TTC ATC GTG GAC ATC TTG CAA TTC TTG GAC ATT GGT
Y   A   K   V   K   E   F   I   V   D   I   L   Q   F   L   D   I   G
     279         288         297         306         315         324

CCT GAT GTC ACC CGA GTG GGC CTG CTC CAA TAT GGC AGC ACT GTC AAG AAT GAG
P   D   V   T   R   V   G   L   L   Q   Y   G   S   T   V   K   N   E
     333         342         351         360         369         378
```

FIGURE 1A

| | 387 | | 396 | | 405 | | 414 | | 423 | | 432 |
|---|---|---|---|---|---|---|---|---|---|---|---|
| TTC | TCC | CTC | AAG | ACC | TTC | AAG | AGG | TCC | GAG | GTG | GAG | CGT | GCT | GTC | AAG | AGG |
| F | S | L | K | T | F | K | R | S | E | V | E | R | A | V | K | R |

| | 441 | | 450 | | 459 | | 468 | | 477 | | 486 |
|---|---|---|---|---|---|---|---|---|---|---|---|
| ATG | CGG | CAT | CTG | TCC | ACG | GGC | ACC | ATG | ACC | GGG | CTG | GCC | ATC | CAG | TAT | GCC | CTG |
| M | R | H | L | S | T | G | T | M | T | G | L | A | I | Q | Y | A | L |

| | 495 | | 504 | | 513 | | 522 | | 531 | | 540 |
|---|---|---|---|---|---|---|---|---|---|---|---|
| AAC | ATC | GCA | TTC | TCA | GAA | GCA | GAG | GGG | GCC | CGG | CCC | CTG | AGG | GAG | AAT | GTG | CCA |
| N | I | A | F | S | E | A | E | G | A | R | P | L | R | E | N | V | P |

| | 549 | | 558 | | 567 | | 576 | | 585 | | 594 |
|---|---|---|---|---|---|---|---|---|---|---|---|
| CGG | GTC | ATA | ATG | ATC | GTG | ACA | GAT | GGG | AGA | CCT | CAG | GAC | TCC | GTG | GCC | GAG | GTG |
| R | V | I | M | I | V | T | D | G | R | P | Q | D | S | V | A | E | V |

| | 603 | | 612 | | 621 | | 630 | | 639 | | 648 |
|---|---|---|---|---|---|---|---|---|---|---|---|
| GCT | GCT | AAG | GCA | CGG | GAC | ACG | GGC | ATC | CTA | ATC | TTT | GCC | ATT | GGT | GTG | GGC | CAG |
| A | A | K | A | R | D | T | G | I | L | I | F | A | I | G | V | G | Q |

| | 657 | | 666 | | 675 | | 684 | | 693 | | 702 |
|---|---|---|---|---|---|---|---|---|---|---|---|
| GAC | TTC | AAC | ACC | TTG | AAG | TCC | ATT | GGG | AGT | GAG | CCC | CAT | GAG | GAC | CAT | GTC |
| D | F | N | T | L | K | S | I | G | S | E | P | H | E | D | H | V |

| | 711 | | 720 | | 729 | | 738 | | 747 | | 756 |
|---|---|---|---|---|---|---|---|---|---|---|---|
| TTC | CTT | GTG | GCC | AAT | TTC | AGC | CAG | ATT | GAG | ACG | CTG | ACC | TCC | GTG | TTC | CAG | AAG |
| F | L | V | A | N | F | S | Q | I | E | T | L | T | S | V | F | Q | K |

FIGURE 1B

```
       765        774        783        792        801        810
AAG TTG TGC ACG GCC CAC ATG TGC AGC ACC CTG GAG CAT AAC TGT GCC CAC TTC
 K   L   C   T   A   H   M   C   S   T   L   E   H   N   C   A   H   F 819        828        837        846        855        864
TGC ATC AAC ATC CCT GGC TCA TAC TGC GTC TGC AGG TGC AAA CAA GGC TAC ATT CTC
 C   I   N   I   P   G   S   Y   C   V   C   R   C   K   Q   G   Y   I   L 873        882        891        900        909        918
AAC TCG GAT CAG ACG ACT TGC AGA ATC CAG GAT CTG TGT GCC ATG GAG GAC CAC
 N   S   D   Q   T   T   C   R   I   Q   D   L   C   A   M   E   D   H 927        936        945        954        963        972
AAC TGT GAG CAG CTC TGT GTG AAT GTG CCG GGC TTC GTC TGC CAG TGC TAC
 N   C   E   Q   L   C   V   N   V   P   G   F   V   C   Q   C   Y 981        990        999       1008       1017       1026
AGT GGC TAC GCC CTG GCT GAG GAT GGG AAG AGG TGT GTG GCT GTG GAC TAC TGT
 S   G   Y   A   L   A   E   D   G   K   R   C   V   A   V   D   Y   C 1035       1044       1053       1062       1071       1080
GCC TCA GAA AAC CAC GGA TGT GAA CAT GAG CAT GAG TGT GTA AAT GCT GAT GGC TCC TAC
 A   S   E   N   H   G   C   E   H   E   C   V   N   A   D   G   S   Y 1089       1098       1107       1116       1125       1134
CTT TGC CAG TGC CAT GAA GGA TTT GCT CTT AAC CCA GAT AAA AAA ACG TGC ACA
 L   C   Q   C   H   E   G   F   A   L   N   P   D   K   K   T   C   T
```

FIGURE 1C

```
        1143              1152              1161              1170              1179              1188
AAG ATA GAC TAC TGT GCC TCA TCT AAT CAC GGA TGT CAG CAC GAG TGT GTT AAC
 K   I   D   Y   C   A   S   S   N   H   G   C   Q   H   E   C   V   N
        1197              1206              1215              1224              1233              1242
ACA GAT GAT TCC TAT TCC TGC CAC CTG AAA GGC TTT ACC CTG AAT CCA GAT
 T   D   D   S   Y   S   C   H   L   K   G   F   T   L   N   P   D
        1251              1260              1269              1278              1287              1296
AAG AAA ACC TGC AGA AGG ATC AAC TAC TGT GCA CTG AAC AAA CCG GGC TGT GAG
 K   K   T   C   R   R   I   N   Y   C   A   L   N   K   P   G   C   E
        1305              1314              1323              1332              1341              1350
CAT GAG TGC GTC AAC ATG GAG GAG AGC TAC TAC TGC CGA GTG GAC CAC CGT GGC TAC
 H   E   C   V   N   M   E   E   S   Y   Y   C   R   V   D   H   R   G   Y
        1359              1368              1377              1386              1395              1404
ACT CTG GAC CCC AAT GGC AAA ACC TGC AGC CGA GTG GAC CAC TGT GCA CAG CAG
 T   L   D   P   N   G   K   T   C   S   R   V   D   H   C   A   Q   Q
        1413              1422              1431              1440              1449              1458
GAC CAT GGC TGT GAG CAG CTG TGT CTG AAC ACG GAG GAT TCC TTC GTC TGC CAG
 D   H   G   C   E   Q   L   C   L   N   T   E   D   S   F   V   C   Q
        1467              1476              1485              1494              1503              1512
TGC TCA GAA GGC TTC CTC ATC AAC GAG GAC CTC AAG ACC TGC TCC CGG GTG GAT
 C   S   E   G   F   L   I   N   E   D   L   K   T   C   S   R   V   D

FIGURE 1D
```

```
              1521           1530           1539        1548           1557           1566
TAC TGC CTG AGT GAC CAT GGT TGT GAA TAC TCC TGT GTC AAC ATG GAC AGA
 Y   C   L   S   D   H   G   C   E   Y   S   C   V   N   M   D   R 1575           1584           1593        1602           1611           1620
TCC TTT GCC TGT CAG TGT CCT GAG GGA CAC GTG CTC CGC AGC GAT GGG AAG ACG
 S   F   A   C   Q   C   P   E   G   H   V   L   R   S   D   G   K   T 1629           1638           1647        1656           1665           1674
TGT GCA AAA TTG GAC TCT TGT GCT CTG GGG GAC CAC GGT TGT GAA CAT TCG TGT
 C   A   K   L   D   S   C   A   L   G   D   H   G   C   E   H   S   C 1683           1692           1701        1710           1719           1728
GTA AGC AGT GAA GAT TCG TTT GTG TGC CAG TGC TTT GAA GGT TAT ATA CTC CGT
 V   S   S   E   D   S   F   V   C   Q   C   F   E   G   Y   I   L   R 1737           1746           1755        1764           1773           1782
GAA GAT GGA AAA ACC TGC AGA AGG AAA GAT GTC TGC CAA GCT ATA GAC CAT GGC
 E   D   G   K   T   C   R   R   K   D   V   C   Q   A   I   D   H   G 1791           1800           1809        1818           1827           1836
TGT GAA CAC ATT TGT GTG AAC AGT GAC GAC TCA TAC ACG TGC GAG TGC TTG GAG
 C   E   H   I   C   V   N   S   D   D   S   Y   T   C   E   C   L   E 1845           1854           1863        1872           1881           1890
GGA TTC CGG CTC GCT GAG GAT GGG AAA CGC TGC CGA AGA AGG ATG TCT GCA AAT
 G   F   R   L   A   E   D   G   K   R   C   R   R   R   M   S   A   N
```

FIGURE 1E

```
     1899            1908            1917       1926           1935            1944
CAA CCC ACC ATG GCT GCG AAC ACA TTT GTG TTA ATA ATG GGA ATT CCT ACA TCT
 Q   P   T   M   A   A   N   T   F   V   L   I   M   G   I   P   T   S 1953            1962            1971       1980           1989            1998
GCA AAT GCT CAG AGG GAT TTG TTC TAG CTG AGG ACG GAA GAC GGT GCA AGA AAT
 A   N   A   Q   R   D   L   F 2007            2016            2025       2034           2043            2052
GCA CTG AAG GCC CAA TTG ACC TGG TCT TTG TGA TCG ATG GAT CCA AGA GTC TTG 2061            2070            2079       2088           2097            2106
GAG AAG AGA ATT TTG AGG TCG TGA AGC AGT TTG TCA CTG GAA TTA TAG ATT CCT 2115            2124            2133       2142           2151            2160
TGA CAA TTT CCC CCA AAG CCG CTC GAG TGG GGC TGC TCC AGT ATT CCA CAC AGG 2169            2178            2187       2196           2205            2214
TCC ACA CAG AGT TCA CTC TGA GAA ACT TCA ACT CAG CCA AAG ACA TGA AAA AAG 2223            2232            2241       2250           2259            2268
CCG TGG CCC ACA TGA AAT ACA TGG GAA AGG GCT CTA TGA CTG GGC TGG CCC TGA 2277            2286            2295       2304           2313            2322
AAC ACA TGT TTG AGA GAA GTT TTA CCC AAG GAG AAG GGG CCA GGC CCC TTT CCA
```

FIGURE 1F

```
                    2331           2340           2349      2358           2367           2376
               CAA GGG TGC CCA GAG CAG CCA TTG TGT TCA CCG ACG GAC GGG CTC AGG ATG ACG
     2385           2394           2403           2412           2421           2430
TCT CCG AGT GGG CCA GTA AAG CCA AGG CCA ATG GTA TCA CTA TGT ATG CTG TTG
     2439           2448           2457           2466           2475           2484
GGG TAG GAA AAG CCA TTG AGG AGG AAC TAC AAG AGA TTG CCT CTG AGC CCA CAA
     2493           2502           2511           2520           2529           2538
ACA AGC ATC TCT TCT ATG CCG AAG ACT TCA GCA CAA TGG ATG AGA TAA GTG AAA
     2547           2556           2565           2574           2583           2592
AAC TCA AGA AAG GCA TCT GTG AAG CTC TAG AAG ACT CCG ATG GAA GAC AGG ACT
     2601           2610           2619           2628           2637           2646
CTC CAG CAG GGG AAC TGC CAA AAA CGG TCC AAC AGC CAA CAG TGC AAC ACA GAT
     2655           2664           2673           2682           2691           2700
ATC TGT TTG AAG AAG ACA ATC TTT TAC GGT CTA CAC AAA AGC TTT CCC ATT CAA
     2709           2718           2727           2736           2745           2754
CAA AAC CTT CAG GAA GCC CTT TGG AAG AAA AAC ACG ATC AAT GCA AAT GTG AAA
     2763           2772           2781           2790           2799           2808
ACC TTA TAA TGT TCC AGA ACC TTG CAA ACG AAG AAG TAA GAA AAT TAA CAC AGC

FIGURE 1G
```

```
       2817            2826            2835            2844            2853            2862
GCT TAG AAG AAA TGA CAC AGA GAA TGG AAG CCC TGG AAA ATC GCC TGA GAT ACA
       2871            2880            2889            2898            2907            2916
GAT GAA GAT TAG AAA TCG CGA CAC ATT TGT AGT CAT TGT ATC ACG GAT TAC AAT
       2925            2934            2943            2952            2961            2970
GAA CGC AGT GCA GAG CCC CAA AGC TCA GGC TAT TGT TAA ATC AAT AAT GTT GTG
       2979            2988            2997            3006            3015            3024
AAG TAA AAC AAT CAG TAC TGA GAA ACC TGG TTT GCC ACA GAA CAA AGA CAA GAA
       3033            3042            3051            3060            3069            3078
GTA TAC ACT AAC TTG TAT AAA TTT ATC TAG GAA AAA AAT CCT TCA GAA TTC TAA
       3087            3096            3105            3114            3123            3132
GAT GAA TTT ACC AGG TGA GAA ATA AGC TAT GCA AGG TAT TTT GTA ATA TAC
       3141            3150            3159            3168            3177            3186
TGT CAC AAC TTG CTT CTG CCT CAT CCT GCC TTA GTG TGC AAT CTC ATT TGA
       3195            3204            3213            3222            3231            3240
CTA TAC GAT AAA GTT TGC ACA GTC TTA CTT CTG TAG AAC ACT GGC CAT AGG AAA
       3249            3258            3267            3276            3285            3294
TGC TGT TTT GTA CTG GAC TTT ACC TTG ATA TAT GTA TAT GGA TGT ATG CAT
```

FIGURE 1H

```
        3303            3312            3321            3330            3339            3348
AAA ATC ATA GGA CAT ATG TAC TTG TGG AAC AAG TTG GAT TTT TTA TAC AAT ATT
        3357            3366
AAA ATT CAC CAC TTC AAA AAA AAA A 3'
```

| | | |
|---|---|---|
| 180 | V A A K A R D T G I L I F A I G V G Q V | 681719 |
| 180 | V A A K A R N T G I L I F A I G V G Q V | GI 2072792 |
| 164 | V S A R A R A S G V E L F A I G V G S V | GI 1732121 |

| | | |
|---|---|---|
| 200 | D F N T L K S I G S E P H E D H V F L V | 681719 |
| 200 | D L N T L K A I G S E P H K D H V F L V | GI 2072792 |
| 184 | D K A T L R Q I A S E P Q D E H V D Y V | GI 1732121 |

| | | |
|---|---|---|
| 220 | A N F S Q I E T L T S V F Q K K L C T A | 681719 |
| 220 | A N F S Q I E S L T S V F Q N K L C T V | GI 2072792 |
| 204 | E S Y S V I E K L S R K F Q E A F C V - | GI 1732121 |

| | | |
|---|---|---|
| 240 | H M C S T L E H N C A H F C I N I P G S | 681719 |
| 240 | H M C S V L E H N C A H F C L N T P G S | GI 2072792 |
| 223 | - - - - - - - - - - - - - - - - - - - - | GI 1732121 |

| | | |
|---|---|---|
| 260 | Y V C R C K Q G Y I L N S D Q T T C R I | 681719 |
| 260 | Y I C K C K Q G Y I L S T D Q K T C R I | GI 2072792 |
| 223 | - - - - - - - - - - - - - - - - - - - V | GI 1732121 |

| | | |
|---|---|---|
| 280 | Q D L C A M E D H N C E Q L C V N V P G | 681719 |
| 280 | Q D L C A T E D H G C E Q L C V N M L G | GI 2072792 |
| 224 | S D L C A T G D H D C E Q V C I S S P G | GI 1732121 |

| | | |
|---|---|---|
| 300 | S F V C Q C Y S G Y A L A E D G K R C V | 681719 |
| 300 | S F V C Q C Y S G Y T L A E D G K R C T | GI 2072792 |
| 244 | S Y T C A C - - - - - - - - - - - - - - | GI 1732121 |

| | | |
|---|---|---|
| 320 | A V D Y C A S E N H G C E H E C V N A D | 681719 |
| 320 | A M D Y C A S E N H G C E H E C V N A E | GI 2072792 |
| 250 | - - - - - - - - - - - - - - - - - - - - | GI 1732121 |

| | | |
|---|---|---|
| 340 | G S Y L C Q C H E G F A L N P D K K T C | 681719 |
| 340 | S S Y L C R C H E G F A L N S D K K T C | GI 2072792 |
| 250 | - - - - - - H E G F T L N S D G K T C | GI 1732121 |

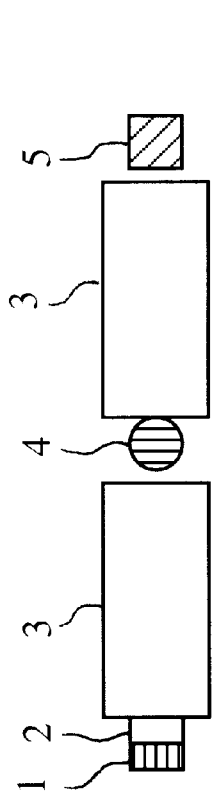
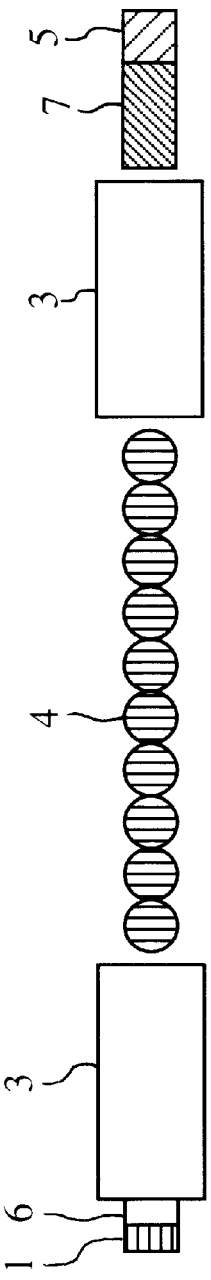
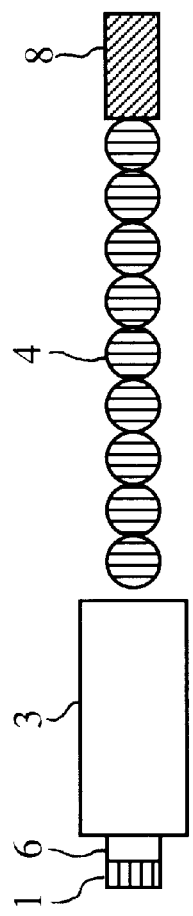
FIGURE 4A
Prior Art
FIGURE 4B
Prior Art
FIGURE 4C

HUMAN MATRILIN-3

FIELD OF THE INVENTION

This invention relates to nucleic acid and amino acid sequences of a human matrilin-3 and to the use of these sequences in the diagnosis, prevention, and treatment of developmental, vesicle trafficking, neoplastic, and immunological disorders.

BACKGROUND OF THE INVENTION

Many eukaryotic cells are enveloped by an extracellular matrix of proteins that provide structural support, cell and tissue identity, and autocrine, paracrine and juxtacrine properties for the cell within its environment (McGowan, S. E. (1992) FASEB J. 6: 2895–2904). The diverse biochemistry of extracellular matrix proteins (ECMP) is indicative of the many, often overlapping, roles that are attributed to each distinct molecule (cf. Grant, D. S. and Kleinman, H. K. (1997) EXS 79: 317–333). Whilst a great number of ECMPs have been isolated, it still remains unclear how the majority interact with other ECMPs or with molecules residing within the cell membrane. Many ECMPs have been associated with tissue growth and cell proliferation, others with tissue or cell differentiation, and yet others with cell death (cf. Taipale, J. and Keski-Oja, J. (1997) FASEB J. 11: 51–59; Eleftheriou, C. S. et al. (1991) Mutat. Res. 256: 127–138).

Multidomain or mosaic proteins play an important role in the diverse functions of the extracellular matrix (ECM) in various tissues (Engel, J. et al. (1994) Development (Camb.) (suppl.) 35–42). Cartilage matrix protein (CMP) is an abundant structural component of the ECM in some types of hyaline cartilage. It binds to aggrecan, the large cartilage proteoglycan, and to cartilage collagen fibrils; and it may serve to connect the two major macromolecular networks (Deák, F. et al. (1997) J. Biol. Chem. 272: 9268–9274).

The primary structure of the CMP monomer has been determined from the nucleotide sequences of human and mouse (Jenkins, R. N. et al. (1990) J. Biol. Chem. 265: 19624–19631; Aszódi, A. et al. (1996) Eur. J. Biochem. 236: 970–977). After cleavage of the signal peptide, each monomer of CMP consists of two von Willebrand factor type A (vWFA)-like modules (collagen-binding motifs) separated by an epidermal growth factor (EGF)-like module and followed by a C-terminal domain. CMP transcript is evenly distributed in the developing mouse skeleton and in late gestation follows a zonal distribution paralleling hypertrophy and calcification; extraskeletal expression of CMP mRNA is detected in the eye [Aszodi, A. et al. (supra)].

CMP is one of the simplest members of the vWFA-like module superfamily, a diverse group of proteins sharing high sequence similarity over a segment. The vWFA-like module was first identified as the repeated type A domain of von Willebrand factor and has since been found not only in plasma proteins but also in plasma membrane and ECM proteins (Colombatti, A. and Bonaldo, P. (1991) Blood 77: 2305–2315). Crystal structure analysis of an integrin vWFA-like module has revealed a classic/"Rossmann" fold and suggested a metal ion-dependent adhesion site. This adhesion site is conserved in other vWFA-like modules and can be involved in binding protein ligands (Lee, J.-O. et al. (1995) Cell 80: 631–638).

A second CMP-like protein, matrilin-2, which shares many characteristics of CMP has recently been identified [Deák, et al. (supra)]. Murine matrilin-2 consists of one vWFA-like domain, ten epidermal growth factor (EGF)-like modules and a C-terminal domain which contains a coiled-coil motif. In addition, matrilin-2 has a N-terminal region rich in positively charged amino acid residues. Conserved homologies between the two proteins, CMP and matrilin-2, suggested that CMP be renamed as matrilin-1 [Deák, et al. (supra)]. Murine matrilin-2 differs from matrilin-1 in that it is detected in diverse tissue types. It is most abundant in embryonic limbs; in calvaria, uterus, heart and brain from newborn mice; and in murine fibroblast and rat osteoblast cell lines [Deák, et al. (supra)].

Elevated serum or synovial fluid levels of cartilage-specific markers, such as the cartilage oligomeric matrix protein (COMP) in patients with rheumatoid arthritis and in animal models of osteoarthritis, may be used to predict disease progression (Saxne, T. and Heinegard, D. (1992) Br. J. Rheumatol 31: 583–591; Malemud, C. J. (1993) Curr. Opin. Rheumatol. 5: 494–502). Chondrodysplasias are characterized by abnormal development of articulating joints and bone. Two loci have been linked within several chondrodysplasia pedigrees. Collagen type II, collagen type X, and CMP have been excluded as disease loci, and mutations in COMP have been linked to pseudochondrodysplasia (Loughlin, J. et al. (1994) Hum. Genet. 94: 698–700; Hecht, J. T. et al. (1995) Nat. Genet. 10: 325–329).

The discovery of a new human matrilin-3 and the polynucleotides encoding it satisfies a need in the art by providing new compositions which are useful in the diagnosis, prevention and treatment of developmental, vesicle trafficking, neoplastic, and immunological disorders.

SUMMARY OF THE INVENTION

The invention features a substantially purified polypeptide, human matrilin-3 (MAT-3), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2 or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding MAT-3 under conditions suitable for the expression of the polypeptide; and b) recovering the polypeptide from the host cell culture.

The invention also provides a pharmaceutical composition comprising a substantially purified MAT-3 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which specifically binds to a polypeptide comprising the amino acid sequence of SEQ ID NO:1.

Still further, the invention provides a purified agonist of the polypeptide of SEQ ID NO:1.

The invention also provides a method for treating or preventing a developmental disorder comprising administering to a subject in need of such treatment an effective amount of a pharmaceutical composition comprising purified MAT-3.

The invention also provides a method for treating or preventing a vesicle trafficking disorder comprising administering to a subject in need of such treatment an effective amount of a purified antagonist to MAT-3.

The invention also provides a method for treating or preventing a neoplastic disorder comprising administering to a subject in need of such treatment an effective amount of a purified antagonist to MAT-3.

The invention also provides a method for treating or preventing an immunological disorder comprising administering to a subject in need of such treatment an effective amount of a purified antagonist to MAT-3.

The invention also provides a method for detecting a polynucleotide which encodes MAT-3 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding MAT-3 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, 1E, 1F, 1G, 1H, and 1I show the amino acid sequence (SEQ ID NO:1) and nucleic acid sequence (SEQ ID NO:2) of MAT-3. The alignment was produced using MACDNASIS PRO software (Hitachi Software Engineering Co. Ltd. San Bruno, Calif.).

Figure 2C:
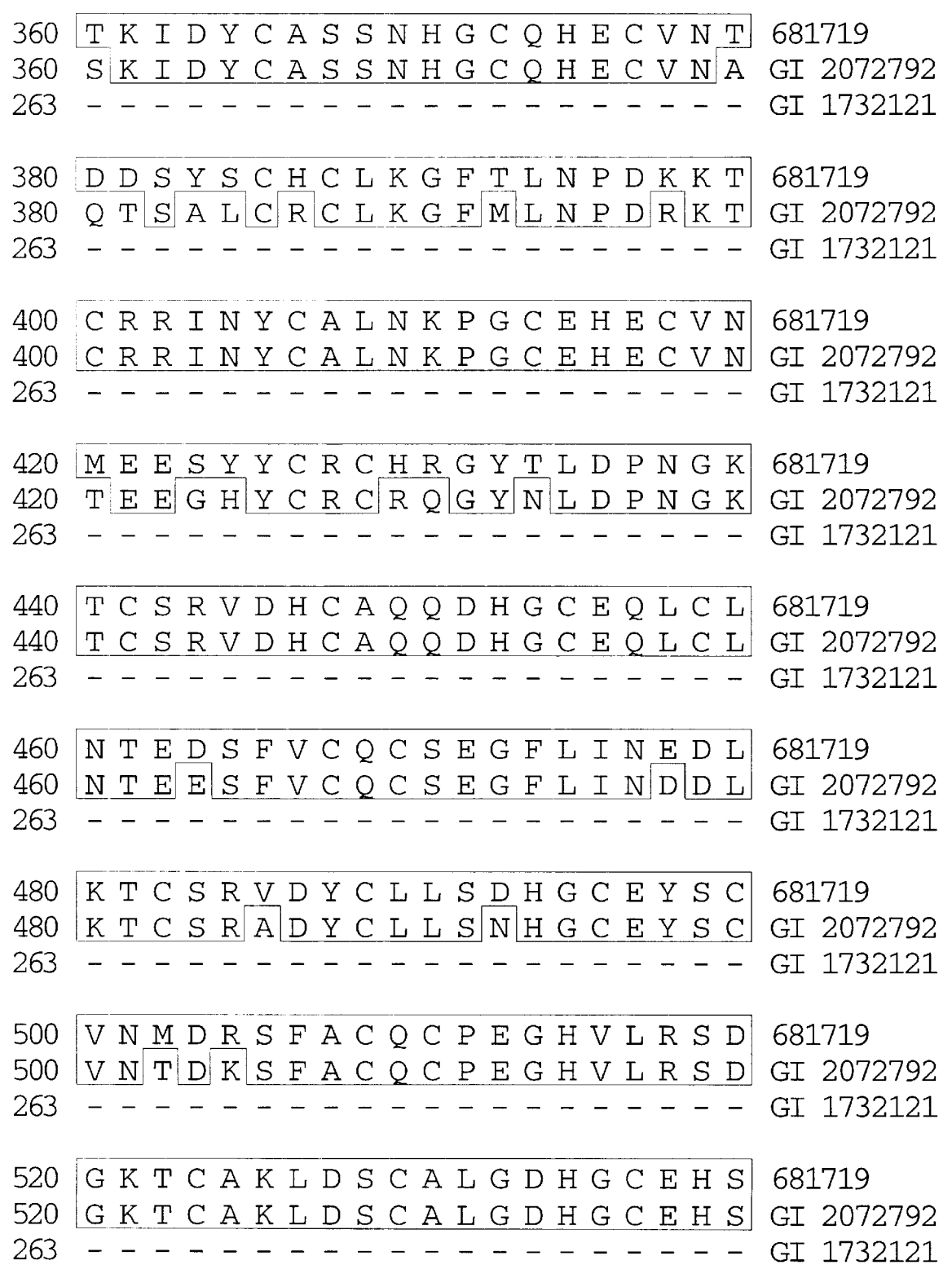
Figure 2D:
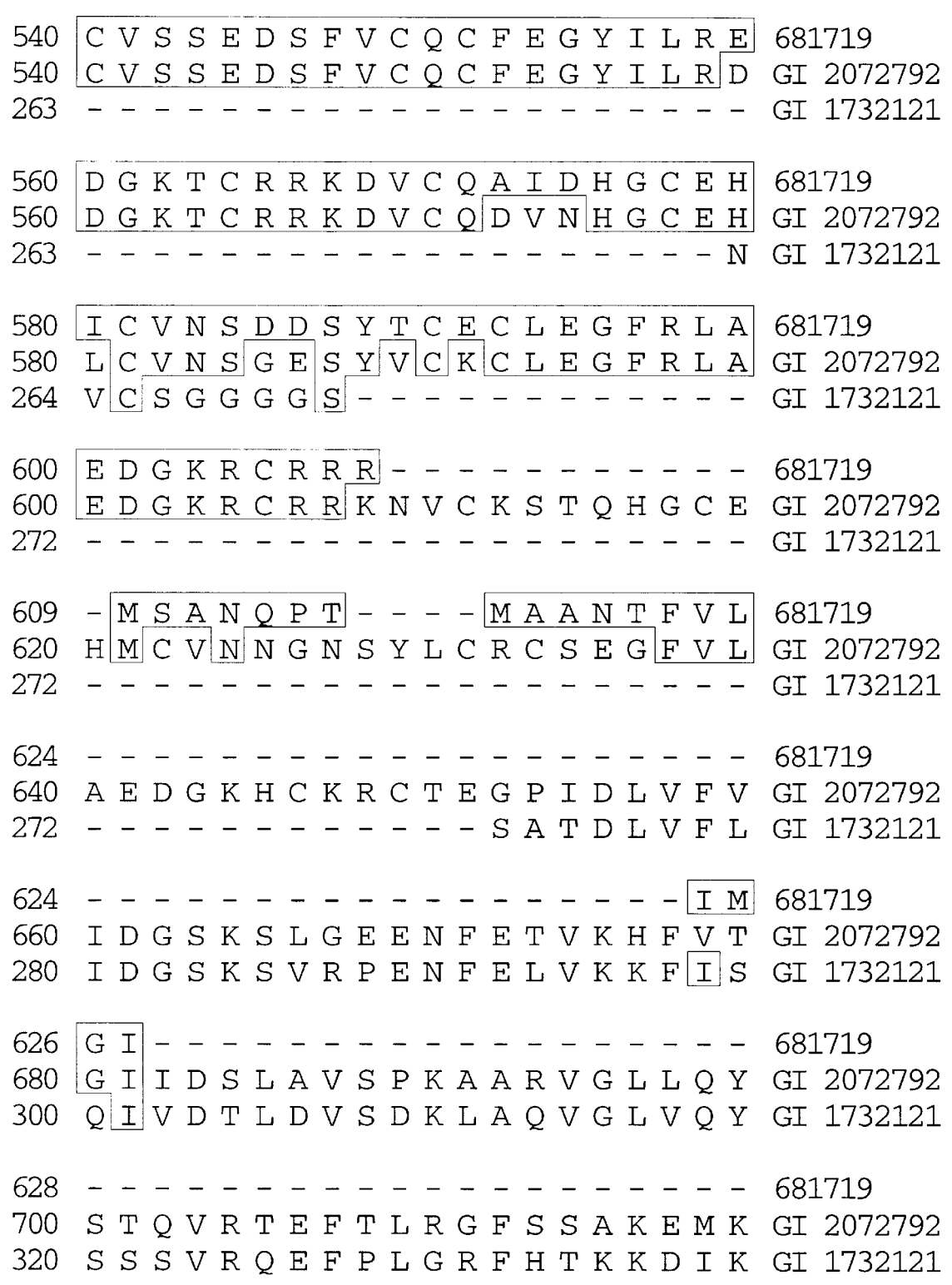
Figure 2E:
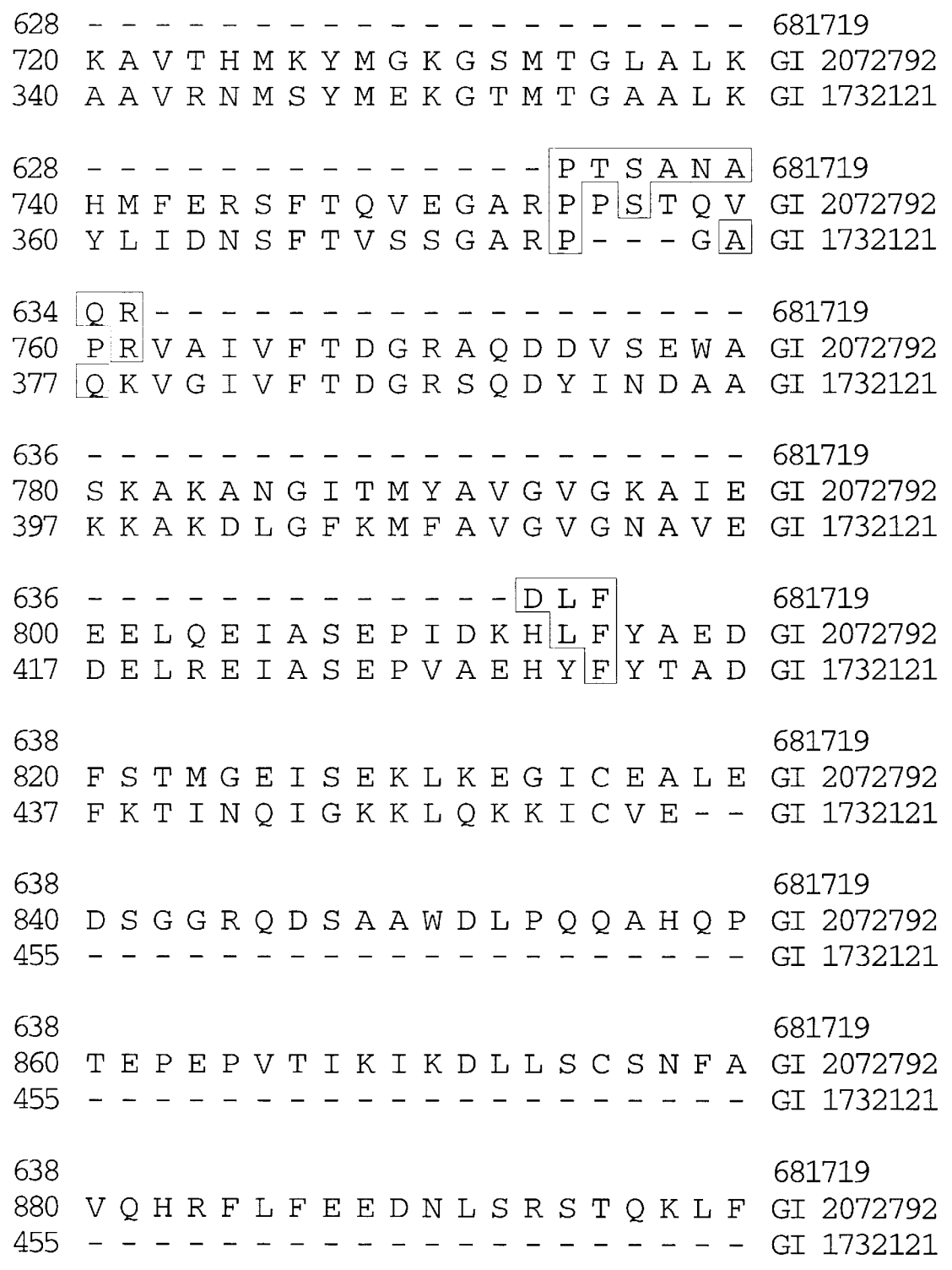
Figure 2F:
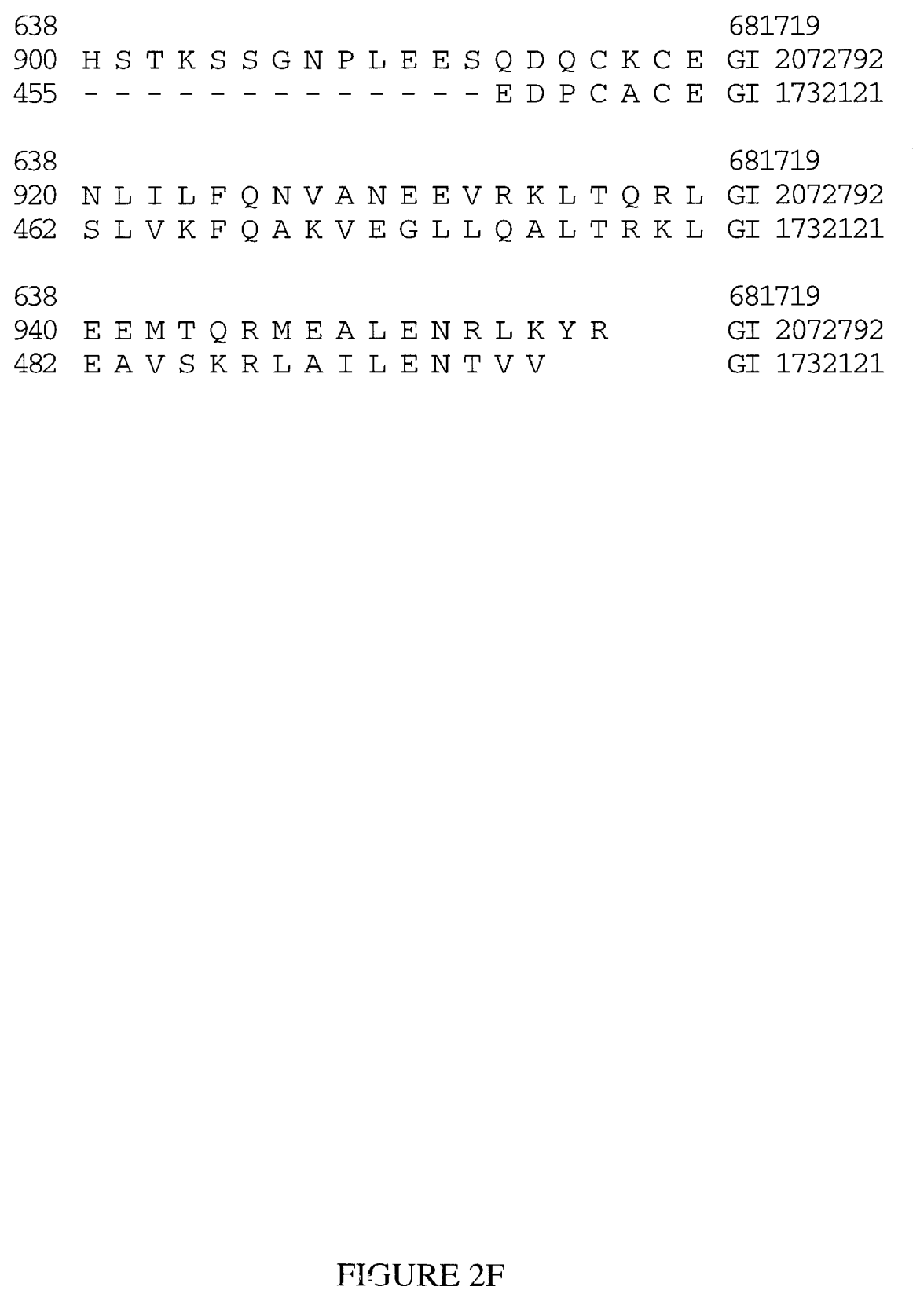

FIGS. 2A, 2B, 2C, 2D, 2E, and 2F show the amino acid sequence alignments among MAT-3 (681719; SEQ ID NO:1), murine matrilin-2 (GI 2072792; SEQ ID NO:3) and human CMP (matrilin-1) (GI 1732121; SEQ ID NO:4), produced using the multisequence alignment program of DNASTAR™ software (DNASTAR Inc, Madison Wis.).

FIGS. 4A, 4B, and 4C compare the known and potential structures of CMP (matrilin-1), matrilin-2, and MAT-3 (matrilin-3), respectively. Numbers refer to the following common structural domains: (1), signal peptide; (2), unique sequence in CMP; (3), vWFA-like module; (4), EGF-like module(s); (5), C-terminal coiled coil α-helix; (6), N-terminal rich in positively charged residues; (7), unique sequence in matrilin-2; (8), unique sequence in MAT-3.

DESCRIPTION OF THE INVENTION

Figure 3A:
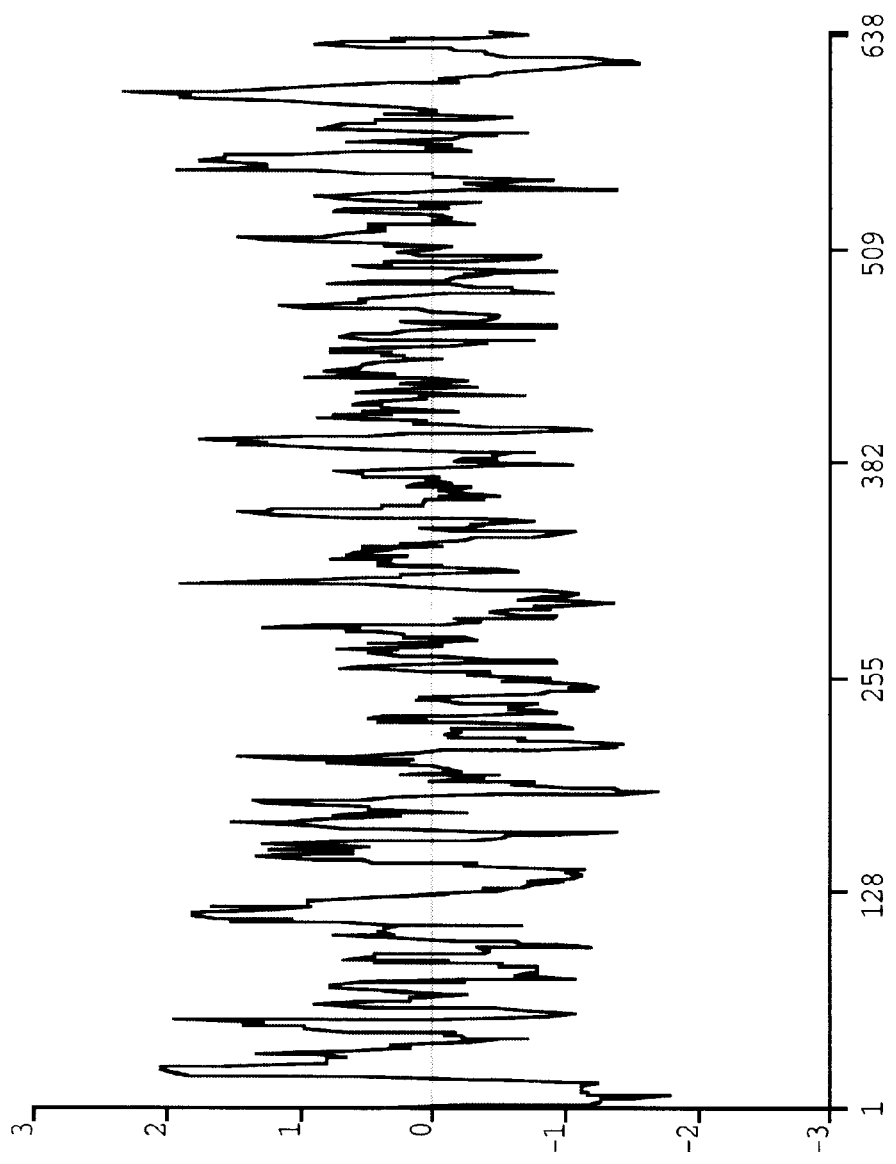
FIGS. 3A and 3B show the hydrophobicity plots for MAT-3, SEQ ID NO:1 and murine matrilin-2 (SEQ ID NO:3), respectively; the positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

MAT-3, as used herein, refers to the amino acid sequences of substantially purified MAT-3 obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to MAT-3, increases or prolongs the duration of the effect of MAT-3. Agonists may include proteins, nucleic acids, carbohydrates, or any other molecules which bind to and modulate the effect of MAT-3.

An "allele" or "allelic sequence", as used herein, is an alternative form of the gene encoding MAT-3. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding MAT-3 as used herein include those with deletions, insertions, or substitutions of different nucleotides resulting in a polynucleotide that encodes the same or a functionally equivalent MAT-3. Included within this definition are polymorphisms which may or may not be readily detectable using a particular oligonucleotide probe of the polynucleotide encoding MAT-3, and improper or unexpected hybridization to alleles, with a locus other than the normal chromosomal locus for the polynucleotide sequence encoding MAT-3. The encoded protein may also be "altered" and contain deletions, insertions, or substitutions of amino acid residues which produce a silent change and result in a functionally equivalent MAT-3. Deliberate amino acid substitutions may be made on the basis of similarity in polarity, charge, solubility, hydrophobicity, hydrophilicity, and/or the amphipathic nature of the residues as long as the biological or immunological activity of MAT-3 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of MAT-3 are preferably about 5 to about 15 amino acids in length and retain the biological activity or the immunological activity of MAT-3. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to MAT-3, decreases the amount or the duration of the effect of the biological or immunological activity of MAT-3. Antagonists may include proteins, nucleic acids, carbohydrates, antibodies or any other molecules which decrease the effect of MAT-3.

As used herein, the term "antibody" refers to intact molecules as well as fragments thereof, such as Fab F(ab')$_2$, and Fv, which are capable of binding the epitopic determinant. Antibodies that bind MAT-3 polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic MAT-3, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding MAT-3 (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR Sequence extension kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding MAT-3 in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to MAT-3 or the encoded MAT-3. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear micro-chromosomes which may contain DNA sequences of 10K to 10M in size and contain all of the elements required for stable mitotic chromosome segregation and maintenance (Harrington, J. J. et al. (1997) Nat Genet. 15: 345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of MAT-3. For example, modulation may cause an increase or a decrease in protein activity, binding characteristics, or any other biological, functional or immunological properties of MAT-3.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8: 53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length MAT-3 and fragments thereof.

The term "sample", as used herein, is used in its broadest sense. A biological sample suspected of containing nucleic acid encoding MAT-3, or fragments thereof, or MAT-3 itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of MAT-3, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human matrilin-3 (hereinafter referred to as "MAT-3"), the polynucleotides encoding MAT-3, and the use of these compositions for the diagnosis, prevention, or treatment of developmental, vesicle trafficking, neoplastic, and immunological disorders.

Nucleic acids encoding the MAT-3 of the present invention were first identified in Incyte Clone 681719 from the uterus cDNA library (UTRSNOT02) using a computer search for amino acid sequence alignments. A consensus sequence, SEQ ID NO:2, was derived from the following overlapping and/or extended nucleic acid sequences: Incyte Clones 681719 (UTRSNOT02), 1816676 (PROSNOT20), 1431166 (SINTBST01), 1720425 (BLADNOT06), 1396388 (THRYNOT03), 1597575 (BRAINOT14), 883007 (THYRNOT02), 1396388 (THYRNOT03), and 881694 (THYRNOT02).

In one embodiment, the invention encompasses a polypeptide comprising the amino acid sequence of SEQ ID NO:1, as shown in FIGS. 1A, 1B, 1C, 1D, 1E, 1F, 1G, 1H, and 1I. MAT-3 is 638 amino acids in length, has a signal peptide sequence (M-1 to A-21), has an N-terminal region rich in positively charged amino acid residues (R-24 to T-44), one potential vWFA-like module between residues E-48 and C-237, and has nine EGF-like modules between residues C-237 and C-605. In addition, MAT-3 has a potential N-glycosylation site at residue N-221; two potential protein kinase A or G phosphorylation sites at residues S-118, and S-610; ten potential casein kinase II phosphorylation sites at residues S-49, S-118, S-149, S-176, S-223, S-243, T-360, S-442, S-483, and S-542; and eight potential protein kinase C phosphorylation sites at residues S-64, T-104, S-110, T-113, T-203, T-276, T-399, and T-563. As shown in FIGS. 2A, 2B, 2C, 2D, 2E, and 2F, MAT-3 has chemical and structural homology with murine matrilin-2 (GI 2072792; SEQ ID NO:3) and with human CMP (GI 1732121; SEQ ID NO:4). In particular, MAT-3 and murine matrilin-2 share 83% identity, share an N-terminal region rich in positively charged amino acid residues, share one potential vWFA-like module, and share eight EGF-like modules. In addition, MAT-3 and matrilin-2 share a potential N-glycosylation site; share one potential protein kinase A or G phosphorylation site; share ten potential casein kinase II phosphorylation sites; and share eight potential protein kinase C phosphorylation sites.

Figure 3B:
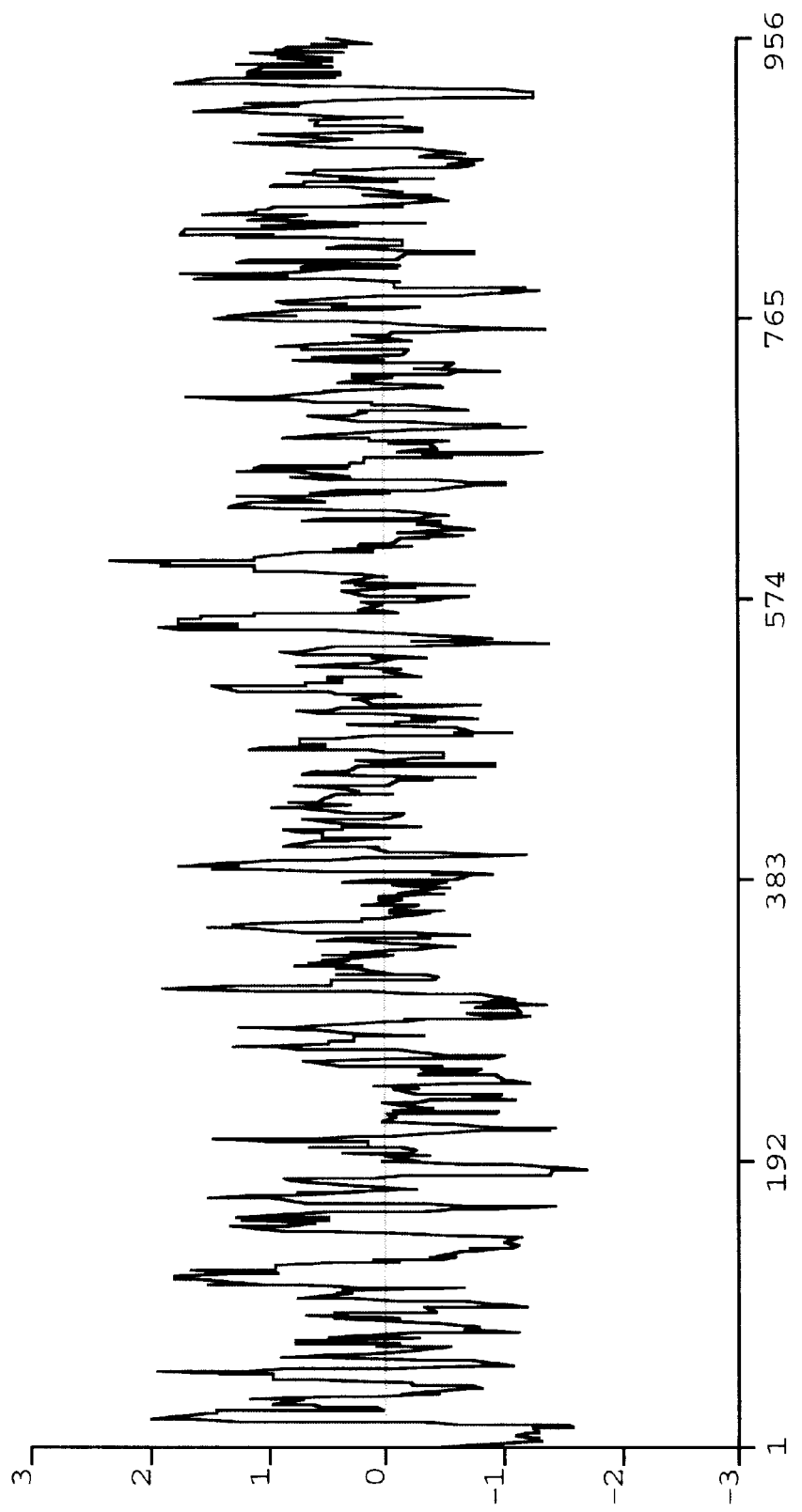

As illustrated by FIGS. 3A and 3B, MAT-3 and residues 1–600 of murine matrilin-2 have rather similar hydrophobicity plots. FIGS. 4A, 4B, and 4C show the structural homologies among matrilin-1 (CMP, prior art), matrilin-2 (prior art), and MAT-3 (matrilin-3), respectively. Each have a signal peptide, have one or two vWPA-like modules, the first of which is followed by one, ten, or nine EGF-like modules, respectively. Each molecule has a unique C-terminal sequence. Northern analysis shows the expression of the sequence of MAT-3 in various libraries, at least 48% of which are immortalized or cancerous, at least at least 76% are secretory tissue, and at least 13% of which involve immune response. Of particular note is the expression of MAT-3 in brain, retina, breast, gut, prostate, testis, thyroid, uterus, and ovary; and in neoplastic and proliferating tissue.

The invention also encompasses MAT-3 variants. A preferred MAT-3 variant is one having at least 80%, and more preferably at least 90%, amino acid sequence identity to the MAT-3 amino acid sequence (SEQ ID NO:1) and which retains at least one biological, immunological or other functional characteristic or activity of MAT-3. A most preferred MAT-3 variant is one having at least 95% amino acid sequence identity to SEQ ID NO:1.

The invention also encompasses polynucleotides which encode MAT-3. Accordingly, any nucleic acid sequence which encodes the amino acid sequence of MAT-3 can be used to produce recombinant molecules which express MAT-3. In a particular embodiment, the invention encompasses the polynucleotide comprising the nucleic acid sequence of SEQ ID NO:2 as shown in FIGS. 1A, 1B, 1C, 1D, 1E, 1F, 1G, 1H, and 1I.

It will be appreciated by those skilled in the art that as a result of the degeneracy of the genetic code, a multitude of nucleotide sequences encoding MAT-3, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring MAT-3, and all such variations are to be considered as being specifically disclosed.

Although nucleotide sequences which encode MAT-3 and its variants are preferably capable of hybridizing to the nucleotide sequence of the naturally occurring MAT-3 under appropriately selected conditions of stringency, it may be advantageous to produce nucleotide sequences encoding MAT-3 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding MAT-3 and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode MAT-3 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding MAT-3 or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152: 399–407) and Kimmel, A. R. (1987; Methods Enzymol. 152: 507–511).

Methods for DNA sequencing which are well known and generally available in the art and may be used to practice any of the embodiments of the invention. The methods may employ such enzymes as the Klenow fragment of DNA polymerase I, SEQUENASE DNA polymerose (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (Gibco/BRL, Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI Catalyst and 373 and 377 DNA SEQUENCERS (Perkin Elmer).

The nucleic acid sequences encoding MAT-3 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2: 318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16: 8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1: 111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19: 3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode MAT-3 may be used in recombinant DNA molecules to direct expression of MAT-3, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express MAT-3.

As will be understood by those of skill in the art, it may be advantageous to produce MAT-3-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter MAT-3 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding MAT-3 may be ligated to a heterologous sequence to encode a fusion protein. For example, to screen peptide libraries for inhibitors of MAT-3 activity, it may be useful to encode a chimeric MAT-3 protein that can be recognized by a commercially available antibody. A fusion protein may also be engineered to contain a cleavage site located between the MAT-3 encoding sequence and the heterologous protein sequence, so that MAT-3 may be cleaved and purified away from the heterologous moiety.

In another embodiment, sequences encoding MAT-3 may be synthesized, in whole or in part, using chemical methods well known in the art (see Caruthers, M. H. et al. (1980) Nucl. Acids Res. Symp. Ser. 7: 215–223, Horn, T. et al. (1980) Nucl. Acids Res. Symp. Ser. 7: 225–232). Alternatively, the protein itself may be produced using chemical methods to synthesize the amino acid sequence of MAT-3, or a fragment thereof. For example, peptide synthesis can be performed using various solid-phase techniques (Roberge, J. Y. et al. (1995) Science 269: 202–204) and automated synthesis may be achieved, for example, using the ABI 431 A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of MAT-3, or any part thereof, may be altered during direct synthesis and/or combined using chemical methods with sequences from other proteins, or any part thereof, to produce a variant polypeptide.

In order to express a biologically active MAT-3, the nucleotide sequences encoding MAT-3 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding MAT-3 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding MAT-3. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding MAT-3, vectors based on SV40 or EBV may be used with an appropriate selectable marker.

In bacterial systems, a number of expression vectors may be selected depending upon the use intended for MAT-3. For example, when large quantities of MAT-3 are needed for the induction of antibodies, vectors which direct high level expression of fusion proteins that are readily purified may be used. Such vectors include, but are not limited to, the multifunctional *E. coli* cloning and expression vectors such as BLUESCRIPT phagemid (Stratagene), in which the sequence encoding MAT-3 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264: 5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153: 516–544.

In cases where plant expression vectors are used, the expression of sequences encoding MAT-3 may be driven by any of a number of promoters. For example, viral promoters such as the 35S and 19S promoters of CaMV may be used alone or in combination with the omega leader sequence from TMV (Takamatsu, N. (1987) EMBO J. 6: 307–311). Alternatively, plant promoters such as the small subunit of RUBISCO or heat shock promoters may be used (Coruzzi, G. et al. (1984) EMBO J. 3: 1671–1680; Broglie, R. et al. (1984) Science 224: 838–843; and Winter, J. et al. (1991) Results Probl. Cell Differ. 17: 85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express MAT-3. For example, in one such system, *Autographa californica* nuclear polyhedrosis virus (AcNPV) is used as a vector to express foreign genes in *Spodoptera frugiperda* cells or in Trichoplusia larvae. The sequences encoding MAT-3 may be cloned into a non-essential region of the virus, such as the polyhedrin gene, and placed under control of the polyhedrin promoter. Successful insertion of MAT-3 will render the polyhedrin gene inactive and produce recombinant virus lacking coat protein. The recombinant viruses may then be used to infect, for example, S. frugiperda cells or Trichoplusia larvae in which MAT-3 may be expressed (Engelhard, E. K. et al. (1994) Proc. Nat. Acad. Sci. 91: 3224–3227).

In mammalian host cells, a number of viral-based expression systems may be utilized. In cases where an adenovirus is used as an expression vector, sequences encoding MAT-3 may be ligated into an adenovirus transcription/translation complex consisting of the late promoter and tripartite leader sequence. Insertion in a non-essential E1 or E3 region of the viral genome may be used to obtain a viable virus which is capable of expressing MAT-3 in infected host cells (Logan, J. and Shenk, T. (1984) Proc. Natl. Acad. Sci. 81: 3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding MAT-3. Such signals include the ATG initiation codon and adjacent sequences. In cases where sequences encoding MAT-3, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20: 125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express MAT-3 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11: 223–32) and adenine phosphoribosyltransferase (Lowy, I. et al. (1980) Cell 22: 817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77: 3567–70); npt, which confers resistance to the aminoglycosides neomycin and G-418 (Colbere-Garapin, F. et al (1981) J. Mol. Biol. 150: 1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85: 8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55: 121–131).

Although the presence/absence of marker gene expression suggests that the gene of interest is also present, its presence and expression may need to be confirmed. For example, if the sequence encoding MAT-3 is inserted within a marker gene sequence, transformed cells containing sequences encoding MAT-3 can be identified by the absence of marker gene function. Alternatively, a marker gene can be placed in tandem with a sequence encoding MAT-3 under the control of a single promoter. Expression of the marker gene in response to induction or selection usually indicates expression of the tandem gene as well.

Alternatively, host cells which contain the nucleic acid sequence encoding MAT-3 and express MAT-3 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding MAT-3 can be detected by DNA-DNA or DNA-RNA hybridization or amplification using probes or fragments or fragments of polynucleotides encoding MAT-3. Nucleic acid amplification based assays involve the use of oligonucleotides or oligomers based on the sequences encoding MAT-3 to detect transformants containing DNA or RNA encoding MAT-3.

A variety of protocols for detecting and measuring the expression of MAT-3, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on MAT-3 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158: 1211–1216).

A wide variety of labels and conjugation techniques are known by those skilled in the art and may be used in various nucleic acid and amino acid assays. Means for producing labeled hybridization or PCR probes for detecting sequences related to polynucleotides encoding MAT-3 include oligolabeling, nick translation, end-labeling or PCR amplification using a labeled nucleotide. Alternatively, the sequences encoding MAT-3, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding MAT-3 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode MAT-3 may be designed to contain signal sequences which direct secretion of MAT-3 through a prokaryotic or eukaryotic cell membrane. Other constructions may be used to join sequences encoding MAT-3 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and MAT-3 may be used to facilitate purification. One such expression vector provides for expression of a fusion protein containing MAT-3 and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying MAT-3 from the fusion protein. A discussion of vectors which contain fusion proteins is provided in Kroll, D. J. et al. (1993; DNA Cell Biol. 12: 441–453).

In addition to recombinant production, fragments of MAT-3 may be produced by direct peptide synthesis using solid-phase techniques (Merrifield J. (1963) J. Am. Chem. Soc. 85: 2149–2154). Protein synthesis may be performed using manual techniques or by automation. Automated synthesis may be achieved, for example, using Applied Biosystems 431A peptide synthesizer (Perkin Elmer). Various fragments of MAT-3 may be chemically synthesized separately and combined using chemical methods to produce the full length molecule.

Therapeutics

Chemical and structural homology exists between MAT-3 and matrilin-2 from mouse (GI 2072793). In addition, MAT-3 is expressed in immortalized or cancerous tissue, in neural, secretory, and fetal tissue, and in proliferating cells. MAT-3 appears to play a role in disorders in which MAT-3 is overexpressed.

Therefore, in one embodiment, MAT-3 or a fragment or derivative thereof may be administered to a subject to treat a developmental disorder. The term "developmental disorder" refers to any disorder associated with development or function of a tissue, organ, or system of a subject, i.e., brain, adrenal gland, kidney, skeletal or reproductive system. Such disorders include, but are not limited to, renal tubular acidosis, anemia, Cushing's syndrome, achondroplastic dwarfism, epilepsy, gonadal dysgenesis, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss.

In another embodiment, a vector capable of expressing MAT-3, or a fragment or a derivative thereof, may also be administered to a subject to treat a developmental disorder including, but not limited to, those described above.

In still another embodiment, an agonist which modulates the activity of MAT-3 may also be administered to a subject to treat a developmental disorder including, but not limited to, those described above.

In one embodiment, an antagonist of MAT-3 may be administered to a subject to treat a vesicle trafficking disorder. Such disorders may include, but are not limited to, cystic fibrosis, glucose-galactose malabsorption syndrome, hypercholesterolemia, diabetes mellitus, diabetes insipidus, hyper- and hypoglycemia, Grave's disease, goiter, Cushing's disease, Addison's disease; gastrointestinal disorders including ulcerative colitis, gastric and duodenal ulcers; and other conditions associated with abnormal vesicle trafficking including AIDS; and allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminth, and protozoal infections. In one aspect, antibodies which specifically bind MAT-3 may be used directly as an antagonist or indirectly as a targeting or delivery mechanism for bringing a pharmaceutical agent to cells or tissue which express MAT-3.

In another embodiment, a vector expressing the complement of the polynucleotide encoding MAT-3 may be administered to a subject to treat or prevent a vesicle trafficking disorder including, but not limited to, those described above.

In one embodiment, an antagonist of MAT-3 may be administered to a subject to prevent or treat a neoplastic disorder. Such disorders may include, but not limited to, adenocarcinoma, leukemia, lymphoma, melanoma, myeloma, sarcoma, teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind MAT-3 may be used directly as an antagonist or indirectly as a targeting or delivery mechanism for bringing a pharmaceutical agent to cells or tissue which express MAT-3.

In another embodiment, a vector expressing the complement of the polynucleotide encoding MAT-3 may be administered to a subject to treat or prevent a neoplastic disorder including, but not limited to, those described above.

In one embodiment, an antagonist of MAT-3 may be administered to a subject to treat an immunological disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. In one aspect, antibodies which specifically bind MAT-3 may be used directly as an antagonist or indirectly as a targeting or delivery mechanism for bringing a pharmaceutical agent to cells or tissue which express MAT-3.

In another embodiment, a vector expressing the complement of the polynucleotide encoding MAT-3 may be administered to a subject to treat or prevent an immunological disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of MAT-3 may be produced using methods which are generally known in the art. In particular, purified MAT-3 may be used to produce antibodies or to screen libraries of pharmaceutical agents to identify those which specifically bind MAT-3.

Antibodies to MAT-3 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with MAT-3 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to MAT-3 have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of MAT-3 amino acids may be fused with those of another protein such as keyhole limpet hemocyanin and antibody produced against the chimeric molecule.

Monoclonal antibodies to MAT-3 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256: 495–497; Kozbor, D. et al. (1985) J. Immunol. Methods 81: 31–42; Cote, R.J. et al. (1983) Proc. Natl. Acad. Sci. 80: 2026–2030; Cole, S. P. et al. (1984) Mol. Cell Biol. 62: 109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81: 6851–6855; Neuberger, M. S. et al. (1984) Nature 312: 604–608; Takeda, S. et al. (1985) Nature 314: 452–454). Alternatively, techniques described for the production of single chain antibodies may be adapted, using methods known in the art, to produce MAT-3-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88: 11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349: 293–299).

Antibody fragments which contain specific binding sites for MAT-3 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254: 1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MAT-3 and its specific antibody. A two-site, monoclonal-based immunoassay utilizing monoclonal antibodies reactive to two non-interfering MAT-3 epitopes is preferred, but a competitive binding assay may also be employed (Maddox, supra).

In another embodiment of the invention, the polynucleotides encoding MAT-3, or any fragment or complement thereof, may be used for therapeutic purposes. In one aspect, the complement of the polynucleotide encoding MAT-3 may be used in situations in which it would be desirable to block the transcription of the mRNA. In particular, cells may be transformed with sequences complementary to polynucleotides encoding MAT-3. Thus, complementary molecules or fragments may be used to modulate MAT-3 activity, or to achieve regulation of gene function. Such technology is now well known in the art, and sense or antisense oligonucleotides or larger fragments, can be designed from various locations along the coding or control regions of sequences encoding MAT-3.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding MAT-3. These techniques are described both in Sambrook et al. (supra) and in Ausubel et al. (supra).

Genes encoding MAT-3 can be turned off by transforming a cell or tissue with expression vectors which express high levels of a polynucleotide or fragment thereof which encodes MAT-3. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding MAT-3 (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding MAT-3.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MAT-3. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15: 462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of MAT-3, antibodies to MAT-3, mimetics, agonists, antagonists, or inhibitors of MAT-3. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of MAT-3, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example MAT-3 or fragments thereof, antibodies of MAT-3, agonists, antagonists or inhibitors of MAT-3, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind MAT-3 may be used for the diagnosis of conditions or diseases characterized by expression of MAT-3, or in assays to monitor patients being treated with MAT-3, agonists, antagonists or inhibitors. The antibodies useful for diagnostic purposes may be prepared in the same manner as those described above for therapeutics. Diagnostic assays for MAT-3 include methods which utilize the antibody and a label to detect MAT-3 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring MAT-3 are known in the art and provide a basis for diagnosing altered or abnormal levels of MAT-3 expression. Normal or standard values for MAT-3 expression are established by combining body fluids or cell extracts taken from normal mammalian subjects, preferably human, with antibody to MAT-3 under conditions suitable for complex formation The amount of standard complex formation may be quantified by various methods, but preferably by photometric, means. Quantities of MAT-3 expressed in subject samples, control and disease, samples from biopsied tissues are compared with the standard values. Deviation between standard and subject values establishes the parameters for diagnosing disease.

In another embodiment of the invention, the polynucleotides encoding MAT-3 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of MAT-3 may be correlated with disease. The diagnostic assay may be used to distinguish between absence, presence, and excess expression of MAT-3, and to monitor regulation of MAT-3 levels during therapeutic intervention.

In one aspect, hybridization with PCR probes which are capable of detecting polynucleotide sequences, including genomic sequences, encoding MAT-3 or closely related molecules, may be used to identify nucleic acid sequences which encode MAT-3. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding MAT-3, alleles, or related sequences.

Probes may also be used for the detection of related sequences, and should preferably contain at least 50% of the nucleotides from any of the MAT-3 encoding sequences. The hybridization probes of the subject invention may be DNA or RNA and derived from the nucleotide sequence of SEQ ID NO:2 or from genomic sequence including promoter, enhancer elements, and introns of the naturally occurring MAT-3.

Means for producing specific hybridization probes for DNAs encoding MAT-3 include the cloning of nucleic acid sequences encoding MAT-3 or MAT-3 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding MAT-3 may be used for the diagnosis of conditions or disorders which are associated with expression of MAT-3. Examples of such conditions or disorders include developmental disorders such as renal tubular acidosis, anemia, Cushing's syndrome, achondroplastic dwarfism, epilepsy, gonadal dysgenesis, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss; vesicle trafficking disorders such as cystic fibrosis, glucose-galactose malabsorption syndrome, hypercholesterolemia, diabetes mellitus, diabetes insipidus, hyper- and hypoglycemia, Grave's disease, goiter, Cushing's disease, Addison's disease; gastrointestinal disorders including ulcerative colitis, gastric and duodenal ulcers; and other conditions associated with vesicle trafficking including AIDS; and allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminth, and protozoal infections; neoplastic disorders such as adenocarcinoma, leukemia, lymphoma, melanoma, myeloma, sarcoma, teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders including those listed above; and Addison's disease, adult respiratory distress syndrome, allergies, atherosclerosis, bronchitis, cholecystitis, Crohn's disease, ulcerative colitis, atopic dermatitis, dermatomyositis, diabetes mellitus, emphysema, erythema nodosum, atrophic gastritis, gout, Graves' disease, hypereosinophilia, irritable bowel syndrome, myocardial or pericardial inflammation, osteoporosis, pancreatitis, polymyositis, Sjogren's syndrome, and autoimmune thyroiditis; complications of cancer, hemodialysis, and extracorporeal circulation; and trauma. The polynucleotide sequences encoding MAT-3 may be used in Southern or northern analysis, dot blot, or other membrane-based technologies; in PCR technologies; or in dipstick, pin, ELISA assays or microarrays utilizing fluids or tissues from patient biopsies to detect altered MAT-3 expression. Such qualitative or quantitative methods are well known in the art.

In a particular aspect, the nucleotide sequences encoding MAT-3 may be useful in assays that detect activation or induction of various cancers, particularly those mentioned above. The nucleotide sequences encoding MAT-3 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding MAT-3 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of MAT-3, a normal or standard profile for expression is established. This may be accomplished by combining body fluids or cell extracts taken from normal subjects, either animal or human, with a sequence, or a fragment thereof, which encodes MAT-3, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MAT-3 may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of MAT-3 include radiolabeling or biotinylating nucleotides, coamplification of a control nucleic acid, and standard curves onto which the experimental results are interpolated (Melby, P. C. et al. (1993) J. Immunol. Methods, 159: 235–244; Duplaa, C. et al. (1993) Anal. Biochem. 212: 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94: 2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251 116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode MAT-3 may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7: 127–134, and Trask, B. J. (1991) Trends Genet. 7: 149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding MAT-3 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336: 577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, MAT-3, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between MAT-3 and the agent being tested, may be measured.

Another technique for drug screening which may be used provides for high throughput screening of compounds having suitable binding affinity to the protein of interest as described in published PCT application WO84/03564. In this method, as applied to MAT-3 large numbers of different small test compounds are synthesized on a solid substrate, such as plastic pins or some other surface. The test compounds are reacted with MAT-3, or fragments thereof, and washed. Bound MAT-3 is then detected by methods well known in the art. Purified MAT-3 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MAT-3 specifically compete with a test compound for binding MAT-3. In this manner, the antibodies can be used to detect the presence of any peptide which shares one or more antigenic determinants with MAT-3.

In additional embodiments, the nucleotide sequences which encode MAT-3 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I UTRSNOT02 cDNA Library Construction

The normal uterine tissue used for uterus cDNA library construction was obtained from a 34 year-old female (Lot #0047A; Mayo Clinic, Rochester, Minn.). Pathology indicated no diagnostic abnormality. The frozen tissue was homogenized and lysed using a POLYTRON homogenizer, PT-3000 (Brinkmann Instruments, Westbury, N.Y.). The reagents and extraction procedures were as supplied in the Stratagene RNA isolation kit (Catalog #200345; Stratagene, La Jolla, Calif.). The lysate was centrifuged over a 5.7 M CsCl cushion using a Beckman SW28 rotor for 18 hours at 25,000 rpm at ambient temperature. The RNA was extracted three times with acid phenol, pH 4.0, precipitated using 0.3 M sodium acetate and 2.5 volumes of ethanol, resuspended in water and DNASE treated for 15 min at 37° C. The RNA was isolated using the OLIGOTEX RNA isolation kit (Quiagen Inc, Chatsworth, Calif.) and used to construct the cDNA library.

The RNA was handled according to recommended protocols in the SUPERSCRIPT plasmid system (Catalog #18248-013, GIBCO BRL), cDNAs fractionated on a SEPHAROSE CL4B column (Catalog #275105, Pharmacia) and ligated into pSPORT I. The pSPORT I plasmid was subsequently transformed into DH5α competent cells (Catalog #18258-012, GIBCO BRL).

II Isolation and Sequencing of cDNA Clones

Plasmid DNA was released from the cells and purified using the REAL Prep 96 Plasmid Kit (Catalog #26173;

QIAGEN, Inc). The recommended protocol was employed except for the following changes: 1) the bacteria were cultured in 1 ml of sterile Terrific Broth (Catalog #22711, GIBco BRL) with carbenicillin at 25 mg/L and glycerol at 0.4%; 2) the cultures were incubated for 19 hours after the wells were inoculated and then lysed with 0.3 ml of lysis buffer; 3) following isopropanol precipitation, the plasmid DNA pellet was resuspended in 0.1 ml of distilled water. After the last step in the protocol, samples were transferred to a Beckman 96-well block for storage at 4° C.

The cDNAs were sequenced by the method of Sanger F. and A. R. Coulson (1975; J. Mol. Biol. 94: 441f), using a Hamilton MICROLAB 2200 (Hamilton, Reno, Nev.) in combination with Peltier thermal cyclers (PTC200 from MJ Research, Watertown, Mass.) and Applied Biosystems 377 DNA sequencing systems; and the reading frame was determined.

III Homology Searching of eDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36: 290–300; Altschul et al. (1990) J. Mol. Biol. 215: 403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5: 35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Atschul (1993; Proc. Nat. Acad. Sci. 90: 5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J.Mol.Evol. 36: 290–300; Altschul, S. F. et al. (1990) J.Mol.Evol. 215: 403–410) are used to search for identical or related molecules in nucleotide databases such as GenBank or the LIFESEQ® database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

% sequence identity x % maximum BLAST score 100
The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding MAT-3 occurs. Abundance and percent abundance are also reported. Abundance directly reflects the number of times a particular transcript is represented in a cDNA library, and percent abundance is abundance divided by the total number of sequences examined in the cDNA library.

V Extension of MAT-3 Encoding Polynucleotides

The nucleic acid sequence of the Incyte Clone 681719 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |

| | |
|---|---|
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK DNA gel purification kit (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 µl of liquid LB/2×Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester, N.Y.) is exposed to the blots, or the blots are placed in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the MAT-3-encoding sequence, or any part thereof, is used to decrease or inhibit expression of naturally occurring MAT-3. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of MAT-3, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the MAT-3-encoding transcript.

IX Expression of MAT-3

Expression of MAT-3 is accomplished by subcloning the cDNAs into appropriate vectors and transforming the vectors into host cells. In this case, the cloning vector is also used to express MAT-3 in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of MAT-3 into the bacterial growth media which can be used directly in the following assay for activity.

X Demonstration of MAT-3 Activity

MAT-3 is measured using a radioimmunoassay for a quantitative determination of 0.2% sodium dodecyl sulphate (SDS), 2.0% Triton X-100-soluble protein (Paulsson, M. and Heinegård, D. (1982) Biochem. J. 207: 207–213). [$^{125}$I]-labelled MAT-3, and non-radioactive test samples, are diluted with 0.1% bovine serum albumin (BSA, fraction V, Sigma Chemical Co., St. Louis, Mich.), 0.4% SDS, 10 mM sodium phosphate buffer, pH 7.4. 50 µl of [$^{125}$I]-labelled MAT-3 (containing 2–3 ng MAT-3, approx 1.5–3.0×10$^4$ cpm total) are mixed with 50 µl of the test sample. 100 µl of 4.0% (w/v) Triton X-100, 10 mM sodium phosphate buffer, pH 7.4, and 100 µl of the diluted primary anti-MAT-3 rabbit antibody in diluent buffer (0.5% BSA, 0.9% NaCl, 0.1% NaN$_3$, 50 mM sodium phosphate buffer, pH 7.5) is added. After mixing, the reagents are incubated for 20 hrs at 4° C. Subsequently, 100 µl of secondary anti-rabbit antibody in diluent buffer, containing 5.0% (w/v) PEG 6000, is added, and reagents incubated for a further 20 hrs at 4° C. The mixture is diluted with 1 ml of diluent buffer before centrifugation (10,000 g). The supernatant is decanted and radioactivity of the pellet determined.

XI Production of MAT-3 Specific Antibodies

MAT-3 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems peptide synthesizer model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring MAT-3 Using Specific Antibodies

Naturally occurring or recombinant MAT-3 is substantially purified by immunoaffinity chromatography using antibodies specific for MAT-3. An immunoaffinity column is constructed by covalently coupling MAT-3 antibody to an activated chromatographic resin, such as CNBr-activated SEPHAROSE resin (Pharmacia & Upjohn). After the coupling, the resin is blocked and washed according to the manufacturer's instructions.

Media containing MAT-3 is passed over the immunoaffinity column, and the column is washed under conditions that allow the preferential absorbance of MAT-3 (e.g., high ionic strength buffers in the presence of detergent). The column is eluted under conditions that disrupt antibody/MAT-3 binding (eg, a buffer of pH 2–3 or a high concentration of a chaotrope, such as urea or thiocyanate ion), and MAT-3 is collected.

XIII Identification of Molecules Which Interact with MAT-3

MAT-3 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled MAT-3, washed and any wells with labeled MAT-3 complex are assayed. Data obtained using different concentrations of MAT-3 are used to calculate values for the number, affinity, and association of MAT-3 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. A composition comprising the polynucleotide sequence of claim 1.

3. A polynucleotide sequence which is fully complementary to the polynucleotide sequence of claim 1.

4. An isolated and purified polynucleotide sequence comprising SEQ ID NO:2.

5. A polynucleotide sequence which is fully complementary to the polynucleotide sequence of claim 4.

6. An expression vector comprising the polynucleotide sequence of claim 1.

7. A host cell containing the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide from the host cell culture.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 638 amino acids
      (B) TYPE: amino acid
      (C) STRANDEDNESS: single
      (D) TOPOLOGY: linear (vii) IMMEDIATE SOURCE:
      (A) LIBRARY: UTRSNOT02
      (B) CLONE: 681719

(xi) SEQUENCE DESCRIPTION: SEQ ID NO:1:

```
Met Glu Lys Met Leu Ala Gly Cys Phe Leu Leu Ile Leu Gly Gln Ile
 1               5                  10                  15

Val Leu Leu Pro Ala Glu Ala Arg Glu Arg Ser Arg Gly Arg Ser Ile
             20                  25                  30

Ser Arg Gly Arg His Ala Arg Thr His Pro Gln Thr Ala Leu Leu Glu
         35                  40                  45

Ser Ser Cys Glu Asn Lys Arg Ala Asp Leu Val Phe Ile Ile Asp Ser
     50                  55                  60

Ser Arg Ser Val Asn Thr His Asp Tyr Ala Lys Val Lys Glu Phe Ile
 65                  70                  75                  80

Val Asp Ile Leu Gln Phe Leu Asp Ile Gly Pro Asp Val Thr Arg Val
                 85                  90                  95

Gly Leu Leu Gln Tyr Gly Ser Thr Val Lys Asn Glu Phe Ser Leu Lys
            100                 105                 110

Thr Phe Lys Arg Lys Ser Glu Val Glu Arg Ala Val Lys Arg Met Arg
        115                 120                 125

His Leu Ser Thr Gly Thr Met Thr Gly Leu Ala Ile Gln Tyr Ala Leu
    130                 135                 140

Asn Ile Ala Phe Ser Glu Ala Glu Gly Ala Arg Pro Leu Arg Glu Asn
145                 150                 155                 160

Val Pro Arg Val Ile Met Ile Val Thr Asp Gly Arg Pro Gln Asp Ser
                165                 170                 175

Val Ala Glu Val Ala Ala Lys Ala Arg Asp Thr Gly Ile Leu Ile Phe
            180                 185                 190

Ala Ile Gly Val Gly Gln Val Asp Phe Asn Thr Leu Lys Ser Ile Gly
        195                 200                 205

Ser Glu Pro His Glu Asp His Val Phe Leu Val Ala Asn Phe Ser Gln
    210                 215                 220

Ile Glu Thr Leu Thr Ser Val Phe Gln Lys Lys Leu Cys Thr Ala His
225                 230                 235                 240

Met Cys Ser Thr Leu Glu His Asn Cys Ala His Phe Cys Ile Asn Ile
                245                 250                 255

Pro Gly Ser Tyr Val Cys Arg Cys Lys Gln Gly Tyr Ile Leu Asn Ser
            260                 265                 270

Asp Gln Thr Thr Cys Arg Ile Gln Asp Leu Cys Ala Met Glu Asp His
        275                 280                 285

Asn Cys Glu Gln Leu Cys Val Asn Val Pro Gly Ser Phe Val Cys Gln
    290                 295                 300

Cys Tyr Ser Gly Tyr Ala Leu Ala Glu Asp Gly Lys Arg Cys Val Ala
```

```
305                 310                 315                 320
Val Asp Tyr Cys Ala Ser Glu Asn His Gly Cys Glu His Glu Cys Val
                325                 330                 335

Asn Ala Asp Gly Ser Tyr Leu Cys Gln Cys His Glu Gly Phe Ala Leu
            340                 345                 350

Asn Pro Asp Lys Lys Thr Cys Thr Lys Ile Asp Tyr Cys Ala Ser Ser
            355                 360                 365

Asn His Gly Cys Gln His Glu Cys Val Asn Thr Asp Asp Ser Tyr Ser
        370                 375                 380

Cys His Cys Leu Lys Gly Phe Thr Leu Asn Pro Asp Lys Lys Thr Cys
385                 390                 395                 400

Arg Arg Ile Asn Tyr Cys Ala Leu Asn Lys Pro Gly Cys Glu His Glu
                405                 410                 415

Cys Val Asn Met Glu Glu Ser Tyr Tyr Cys Arg Cys His Arg Gly Tyr
            420                 425                 430

Thr Leu Asp Pro Asn Gly Lys Thr Cys Ser Arg Val Asp His Cys Ala
            435                 440                 445

Gln Gln Asp His Gly Cys Glu Gln Leu Cys Leu Asn Thr Glu Asp Ser
        450                 455                 460

Phe Val Cys Gln Cys Ser Glu Gly Phe Leu Ile Asn Glu Asp Leu Lys
465                 470                 475                 480

Thr Cys Ser Arg Val Asp Tyr Cys Leu Leu Ser Asp His Gly Cys Glu
                485                 490                 495

Tyr Ser Cys Val Asn Met Asp Arg Ser Phe Ala Cys Gln Cys Pro Glu
            500                 505                 510

Gly His Val Leu Arg Ser Asp Gly Lys Thr Cys Ala Lys Leu Asp Ser
        515                 520                 525

Cys Ala Leu Gly Asp His Gly Cys Glu His Ser Cys Val Ser Ser Glu
530                 535                 540

Asp Ser Phe Val Cys Gln Cys Phe Glu Gly Tyr Ile Leu Arg Glu Asp
545                 550                 555                 560

Gly Lys Thr Cys Arg Arg Lys Asp Val Cys Gln Ala Ile Asp His Gly
                565                 570                 575

Cys Glu His Ile Cys Val Asn Ser Asp Asp Ser Tyr Thr Cys Glu Cys
            580                 585                 590

Leu Glu Gly Phe Arg Leu Ala Glu Asp Gly Lys Arg Cys Arg Arg Arg
        595                 600                 605

Met Ser Ala Asn Gln Pro Thr Met Ala Ala Asn Thr Phe Val Leu Ile
        610                 615                 620

Met Gly Ile Pro Thr Ser Ala Asn Ala Gln Arg Asp Leu Phe
625                 630                 635
```

(2) INFORMATION FOR SEQ ID NO:2:

(i) SEQUENCE CHARACTERISTICS:
        (A) LENGTH: 3373 base pairs
        (B) TYPE: nucleic acid
        (C) STRANDEDNESS: single
        (D) TOPOLOGY: linear (vii) IMMEDIATE SOURCE:
        (A) LIBRARY: UTRSNOT02
        (B) CLONE: 681719

(xi) SEQUENCE DESCRIPTION: SEQ ID NO:2:

```
GGTAGCCGAC GCGCCGGCCG GCGCGTGACC TTGCCCCTCT TGCTCGCCTT GAAAATGGAA      60

AAGATGCTCG CAGGCTGCTT TCTGCTGATC CTCGGACAGA TCGTCCTCCT CCCTGCCGAG     120
```

```
GCCAGGGAGC GGTCACGTGG GAGGTCCATC TCTAGGGGCA GACACGCTCG GACCCACCCG    180

CAGACGGCCC TTCTGGAGAG TTCCTGTGAG AACAAGCGGG CAGACCTGGT TTTCATCATT    240

GACAGCTCTC GCAGTGTCAA CACCCATGAC TATGCAAAGG TCAAGGAGTT CATCGTGGAC    300

ATCTTGCAAT TCTTGGACAT TGGTCCTGAT GTCACCCGAG TGGGCCTGCT CCAATATGGC    360

AGCACTGTCA AGAATGAGTT CTCCCTCAAG ACCTTCAAGA GGAAGTCCGA GGTGGAGCGT    420

GCTGTCAAGA GGATGCGGCA TCTGTCCACG GCACCATGA CCGGGCTGGC CATCCAGTAT    480

GCCCTGAACA TCGCATTCTC AGAAGCAGAG GGGGCCCGGC CCCTGAGGGA GAATGTGCCA    540

CGGGTCATAA TGATCGTGAC AGATGGGAGA CCTCAGGACT CCGTGGCCGA GGTGGCTGCT    600

AAGGCACGGG ACACGGGCAT CCTAATCTTT GCCATTGGTG TGGGCCAGGT AGACTTCAAC    660

ACCTTGAAGT CCATTGGGAG TGAGCCCCAT GAGGACCATG TCTTCCTTGT GGCCAATTTC    720

AGCCAGATTG AGACGCTGAC CTCCGTGTTC CAGAAGAAGT TGTGCACGGC CCACATGTGC    780

AGCACCCTGG AGCATAACTG TGCCCACTTC TGCATCAACA TCCCTGGCTC ATACGTCTGC    840

AGGTGCAAAC AAGGCTACAT TCTCAACTCG GATCAGACGA CTTGCAGAAT CCAGGATCTG    900

TGTGCCATGG AGGACCACAA CTGTGAGCAG CTCTGTGTGA ATGTGCCGGG CTCCTTCGTC    960

TGCCAGTGCT ACAGTGGCTA CGCCCTGGCT GAGGATGGGA AGAGGTGTGT GGCTGTGGAC   1020

TACTGTGCCT CAGAAAACCA CGGATGTGAA CATGAGTGTG TAAATGCTGA TGGCTCCTAC   1080

CTTTGCCAGT GCCATGAAGG ATTTGCTCTT AACCCAGATA AAAAAACGTG CACAAAGATA   1140

GACTACTGTG CCTCATCTAA TCACGGATGT CAGCACGAGT GTGTTAACAC AGATGATTCC   1200

TATTCCTGCC ACTGCCTGAA AGGCTTTACC CTGAATCCAG ATAAGAAAAC CTGCAGAAGG   1260

ATCAACTACT GTGCACTGAA CAAACCGGGC TGTGAGCATG AGTGCGTCAA CATGGAGGAG   1320

AGCTACTACT GCCGCTGCCA CCGTGGCTAC ACTCTGGACC CCAATGGCAA AACCTGCAGC   1380

CGAGTGGACC ACTGTGCACA GCAGGACCAT GGCTGTGAGC AGCTGTGTCT GAACACGGAG   1440

GATTCCTTCG TCTGCCAGTG CTCAGAAGGC TTCCTCATCA ACGAGGACCT CAAGACCTGC   1500

TCCCGGGTGG ATTACTGCCT GCTGAGTGAC CATGGTTGTG AATACTCCTG TGTCAACATG   1560

GACAGATCCT TTGCCTGTCA GTGTCCTGAG GGACACGTGC TCCGCAGCGA TGGGAAGACG   1620

TGTGCAAAAT TGGACTCTTG TGCTCTGGGG ACCACGGTT GTGAACATTC GTGTGTAAGC   1680

AGTGAAGATT CGTTTGTGTG CCAGTGCTTT GAAGGTTATA TACTCCGTGA AGATGGAAAA   1740

ACCTGCAGAA GGAAAGATGT CTGCCAAGCT ATAGACCATG GCTGTGAACA CATTTGTGTG   1800

AACAGTGACG ACTCATACAC GTGCGAGTGC TTGGAGGGAT TCCGGCTCGC TGAGGATGGG   1860

AAACGCTGCC GAAGAAGGAT GTCTGCAAAT CAACCCACCA TGGCTGCGAA CACATTTGTG   1920

TTAATAATGG GAATTCCTAC ATCTGCAAAT GCTCAGAGGG ATTTGTTCTA GCTGAGGACG   1980

GAAGACGGTG CAAGAAATGC ACTGAAGGCC CAATTGACCT GGTCTTTGTG ATCGATGGAT   2040

CCAAGAGTCT TGGAGAAGAG AATTTTGAGG TCGTGAAGCA GTTTGTCACT GGAATTATAG   2100

ATTCCTTGAC AATTTCCCCC AAAGCCGCTC GAGTGGGGCT GCTCCAGTAT TCCACACAGG   2160

TCCACACAGA GTTCACTCTG AGAAACTTCA ACTCAGCCAA AGACATGAAA AAGCCGTGG    2220

CCCACATGAA ATACATGGGA AAGGGCTCTA TGACTGGGCT GGCCCTGAAA CACATGTTTG   2280

AGAGAAGTTT TACCCAAGGA GAAGGGGCCA GGCCCCTTTC CACAAGGGTG CCCAGAGCAG   2340

CCATTGTGTT CACCGACGGA CGGGCTCAGG ATGACGTCTC CGAGTGGGCC AGTAAAGCCA   2400

AGGCCAATGG TATCACTATG TATGCTGTTG GGGTAGGAAA AGCCATTGAG GAGGAACTAC   2460

AAGAGATTGC CTCTGAGCCC ACAAACAAGC ATCTCTTCTA TGCCGAAGAC TTCAGCACAA   2520
```

-continued

```
TGGATGAGAT AAGTGAAAAA CTCAAGAAAG GCATCTGTGA AGCTCTAGAA GACTCCGATG    2580

GAAGACAGGA CTCTCCAGCA GGGGAACTGC CAAAAACGGT CCAACAGCCA ACAGTGCAAC    2640

ACAGATATCT GTTTGAAGAA GACAATCTTT TACGGTCTAC ACAAAAGCTT TCCCATTCAA    2700

CAAAACCTTC AGGAAGCCCT TTGGAAGAAA AACACGATCA ATGCAAATGT GAAAACCTTA    2760

TAATGTTCCA GAACCTTGCA AACGAAGAAG TAAGAAAATT AACACAGCGC TTAGAAGAAA    2820

TGACACAGAG AATGGAAGCC CTGGAAAATC GCCTGAGATA CAGATGAAGA TTAGAAATCG    2880

CGACACATTT GTAGTCATTG TATCACGGAT TACAATGAAC GCAGTGCAGA GCCCCAAAGC    2940

TCAGGCTATT GTTAAATCAA TAATGTTGTG AAGTAAAACA ATCAGTACTG AGAAACCTGG    3000

TTTGCCACAG AACAAAGACA AGAAGTATAC ACTAACTTGT ATAAATTTAT CTAGGAAAAA    3060

AATCCTTCAG AATTCTAAGA TGAATTTACC AGGTGAGAAT GAATAAGCTA TGCAAGGTAT    3120

TTTGTAATAT ACTGTGGACA CAACTTGCTT CTGCCTCATC CTGCCTTAGT GTGCAATCTC    3180

ATTTGACTAT ACGATAAAGT TTGCACAGTC TTACTTCTGT AGAACACTGG CCATAGGAAA    3240

TGCTGTTTTT TTGTACTGGA CTTTACCTTG ATATATGTAT ATGGATGTAT GCATAAAATC    3300

ATAGGACATA TGTACTTGTG GAACAAGTTG GATTTTTTAT ACAATATTAA AATTCACCAC    3360

TTCAAAAAAA AAA                                                      3373
```

(2) INFORMATION FOR SEQ ID NO:3:

(i) SEQUENCE CHARACTERISTICS:
        (A) LENGTH: 956 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 2072792

(xi) SEQUENCE DESCRIPTION: SEQ ID NO:3:

```
Met Glu Lys Met Leu Val Gly Cys Leu Leu Met Leu Gly Gln Leu Phe
 1               5                  10                  15

Leu Val Leu Pro Val Asp Gly Arg Glu Arg Pro Gln Ala Arg Phe Pro
            20                  25                  30

Ser Arg Gly Arg His Val Arg Met Tyr Pro Gln Thr Ala Leu Leu Glu
        35                  40                  45

Ser Ser Cys Glu Asn Lys Arg Ala Asp Leu Val Phe Ile Ile Asp Ser
    50                  55                  60

Ser Arg Ser Val Asn Thr Tyr Asp Tyr Ala Lys Val Lys Glu Phe Ile
65                  70                  75                  80

Leu Asp Ile Leu Gln Phe Leu Asp Ile Gly Pro Asp Val Thr Arg Val
                85                  90                  95

Gly Leu Leu Gln Tyr Gly Ser Thr Val Lys Asn Glu Phe Ser Leu Lys
            100                 105                 110

Thr Phe Lys Arg Lys Ser Glu Val Glu Arg Ala Val Lys Arg Met Arg
        115                 120                 125

His Leu Ser Thr Gly Thr Met Thr Gly Leu Ala Ile Gln Tyr Ala Leu
    130                 135                 140

Asn Ile Ala Phe Ser Glu Ala Glu Gly Ala Arg Pro Leu Arg Glu Asn
145                 150                 155                 160

Val Pro Arg Ile Ile Met Ile Val Thr Asp Gly Arg Pro Gln Asp Ser
                165                 170                 175

Val Ala Glu Val Ala Ala Lys Ala Arg Asn Thr Gly Ile Leu Ile Phe
```

-continued

```
                    180                 185                 190
Ala Ile Gly Val Gly Gln Val Asp Leu Asn Thr Leu Lys Ala Ile Gly
                195                 200                 205

Ser Glu Pro His Lys Asp His Val Phe Leu Val Ala Asn Phe Ser Gln
            210                 215                 220

Ile Glu Ser Leu Thr Ser Val Phe Gln Asn Lys Leu Cys Thr Val His
225                 230                 235                 240

Met Cys Ser Val Leu Glu His Asn Cys Ala His Phe Cys Leu Asn Thr
                245                 250                 255

Pro Gly Ser Tyr Ile Cys Lys Cys Lys Gln Gly Tyr Ile Leu Ser Thr
            260                 265                 270

Asp Gln Lys Thr Cys Arg Ile Gln Asp Leu Cys Ala Thr Glu Asp His
            275                 280                 285

Gly Cys Glu Gln Leu Cys Val Asn Met Leu Gly Ser Phe Val Cys Gln
        290                 295                 300

Cys Tyr Ser Gly Tyr Thr Leu Ala Glu Asp Gly Lys Arg Cys Thr Ala
305                 310                 315                 320

Met Asp Tyr Cys Ala Ser Glu Asn His Gly Cys Glu His Glu Cys Val
                325                 330                 335

Asn Ala Glu Ser Ser Tyr Leu Cys Arg Cys His Glu Gly Phe Ala Leu
            340                 345                 350

Asn Ser Asp Lys Lys Thr Cys Ser Lys Ile Asp Tyr Cys Ala Ser Ser
        355                 360                 365

Asn His Gly Cys Gln His Glu Cys Val Asn Ala Gln Thr Ser Ala Leu
        370                 375                 380

Cys Arg Cys Leu Lys Gly Phe Met Leu Asn Pro Asp Arg Lys Thr Cys
385                 390                 395                 400

Arg Arg Ile Asn Tyr Cys Ala Leu Asn Lys Pro Gly Cys Glu His Glu
                405                 410                 415

Cys Val Asn Thr Glu Glu Gly His Tyr Cys Arg Cys Arg Gln Gly Tyr
            420                 425                 430

Asn Leu Asp Pro Asn Gly Lys Thr Cys Ser Arg Val Asp His Cys Ala
        435                 440                 445

Gln Gln Asp His Gly Cys Glu Gln Leu Cys Leu Asn Thr Glu Glu Ser
    450                 455                 460

Phe Val Cys Gln Cys Ser Glu Gly Phe Leu Ile Asn Asp Asp Leu Lys
465                 470                 475                 480

Thr Cys Ser Arg Ala Asp Tyr Cys Leu Leu Ser Asn His Gly Cys Glu
                485                 490                 495

Tyr Ser Cys Val Asn Thr Asp Lys Ser Phe Ala Cys Gln Cys Pro Glu
            500                 505                 510

Gly His Val Leu Arg Ser Asp Gly Lys Thr Cys Ala Lys Leu Asp Ser
        515                 520                 525

Cys Ala Leu Gly Asp His Gly Cys Glu His Ser Cys Val Ser Ser Glu
530                 535                 540

Asp Ser Phe Val Cys Gln Cys Phe Glu Gly Tyr Ile Leu Arg Asp Asp
545                 550                 555                 560

Gly Lys Thr Cys Arg Arg Lys Asp Val Cys Gln Asp Val Asn His Gly
                565                 570                 575

Cys Glu His Leu Cys Val Asn Ser Gly Glu Ser Tyr Val Cys Lys Cys
            580                 585                 590

Leu Glu Gly Phe Arg Leu Ala Glu Asp Gly Lys Arg Cys Arg Arg Lys
        595                 600                 605
```

```
Asn Val Cys Lys Ser Thr Gln His Gly Cys Glu His Met Cys Val Asn
610                 615                 620

Asn Gly Asn Ser Tyr Leu Cys Arg Cys Ser Glu Gly Phe Val Leu Ala
625                 630                 635                 640

Glu Asp Gly Lys His Cys Lys Arg Cys Thr Glu Gly Pro Ile Asp Leu
                645                 650                 655

Val Phe Val Ile Asp Gly Ser Lys Ser Leu Gly Glu Glu Asn Phe Glu
                660                 665                 670

Thr Val Lys His Phe Val Thr Gly Ile Ile Asp Ser Leu Ala Val Ser
            675                 680                 685

Pro Lys Ala Ala Arg Val Gly Leu Leu Gln Tyr Ser Thr Gln Val Arg
690                 695                 700

Thr Glu Phe Thr Leu Arg Gly Phe Ser Ser Ala Lys Glu Met Lys Lys
705                 710                 715                 720

Ala Val Thr His Met Lys Tyr Met Gly Lys Gly Ser Met Thr Gly Leu
                725                 730                 735

Ala Leu Lys His Met Phe Glu Arg Ser Phe Thr Gln Val Glu Gly Ala
            740                 745                 750

Arg Pro Pro Ser Thr Gln Val Pro Arg Val Ala Ile Val Phe Thr Asp
            755                 760                 765

Gly Arg Ala Gln Asp Asp Val Ser Glu Trp Ala Ser Lys Ala Lys Ala
770                 775                 780

Asn Gly Ile Thr Met Tyr Ala Val Gly Val Gly Lys Ala Ile Glu Glu
785                 790                 795                 800

Glu Leu Gln Glu Ile Ala Ser Glu Pro Ile Asp Lys His Leu Phe Tyr
                805                 810                 815

Ala Glu Asp Phe Ser Thr Met Gly Glu Ile Ser Glu Lys Leu Lys Glu
            820                 825                 830

Gly Ile Cys Glu Ala Leu Glu Asp Ser Gly Gly Arg Gln Asp Ser Ala
            835                 840                 845

Ala Trp Asp Leu Pro Gln Gln Ala His Gln Pro Thr Glu Pro Glu Pro
850                 855                 860

Val Thr Ile Lys Ile Lys Asp Leu Leu Ser Cys Ser Asn Phe Ala Val
865                 870                 875                 880

Gln His Arg Phe Leu Phe Glu Glu Asp Asn Leu Ser Arg Ser Thr Gln
                885                 890                 895

Lys Leu Phe His Ser Thr Lys Ser Ser Gly Asn Pro Leu Glu Glu Ser
            900                 905                 910

Gln Asp Gln Cys Lys Cys Glu Asn Leu Ile Leu Phe Gln Asn Val Ala
            915                 920                 925

Asn Glu Glu Val Arg Lys Leu Thr Gln Arg Leu Glu Glu Met Thr Gln
930                 935                 940

Arg Met Glu Ala Leu Glu Asn Arg Leu Lys Tyr Arg
945                 950                 955

(2) INFORMATION FOR SEQ ID NO:4:

(i) SEQUENCE CHARACTERISTICS:
        (A) LENGTH: 496 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1732121

(xi) SEQUENCE DESCRIPTION: SEQ ID NO:4:
```

```
Met Arg Val Leu Ser Gly Thr Ser Leu Met Leu Cys Ser Leu Leu Leu
 1               5                  10                  15

Leu Leu Gln Ala Leu Cys Ser Pro Gly Leu Ala Pro Gln Ser Arg Gly
             20                  25                  30

His Leu Cys Arg Thr Arg Pro Thr Asp Leu Val Phe Val Val Asp Ser
             35                  40                  45

Ser Arg Ser Val Arg Pro Val Glu Phe Glu Lys Val Lys Val Phe Leu
 50                  55                  60

Ser Gln Val Ile Glu Ser Leu Asp Val Gly Pro Asn Ala Thr Arg Val
 65                  70                  75                  80

Gly Met Val Asn Tyr Ala Ser Thr Val Lys Gln Glu Phe Ser Leu Arg
                 85                  90                  95

Ala His Val Ser Lys Ala Ala Leu Leu Gln Ala Val Arg Arg Ile Gln
                 100                 105                 110

Pro Leu Ser Thr Gly Thr Met Thr Gly Leu Ala Ile Gln Phe Ala Ile
             115                 120                 125

Thr Lys Ala Phe Gly Asp Ala Glu Gly Gly Arg Ser Arg Ser Pro Asp
 130                 135                 140

Ile Ser Lys Val Val Ile Val Val Thr Asp Gly Arg Pro Gln Asp Ser
 145                 150                 155                 160

Val Gln Asp Val Ser Ala Arg Ala Arg Ala Ser Gly Val Glu Leu Phe
                 165                 170                 175

Ala Ile Gly Val Gly Ser Val Asp Lys Ala Thr Leu Arg Gln Ile Ala
                 180                 185                 190

Ser Glu Pro Gln Asp Glu His Val Asp Tyr Val Glu Ser Tyr Ser Val
             195                 200                 205

Ile Glu Lys Leu Ser Arg Lys Phe Gln Glu Ala Phe Cys Val Val Ser
 210                 215                 220

Asp Leu Cys Ala Thr Gly Asp His Asp Cys Glu Gln Val Cys Ile Ser
225                 230                 235                 240

Ser Pro Gly Ser Tyr Thr Cys Ala Cys His Glu Gly Phe Thr Leu Asn
                 245                 250                 255

Ser Asp Gly Lys Thr Cys Asn Val Cys Ser Gly Gly Gly Ser Ser
                 260                 265                 270

Ala Thr Asp Leu Val Phe Leu Ile Asp Gly Ser Lys Ser Val Arg Pro
                 275                 280                 285

Glu Asn Phe Glu Leu Val Lys Lys Phe Ile Ser Gln Ile Val Asp Thr
                 290                 295                 300

Leu Asp Val Ser Asp Lys Leu Ala Gln Val Gly Leu Val Gln Tyr Ser
305                 310                 315                 320

Ser Ser Val Arg Gln Glu Phe Pro Leu Gly Arg Phe His Thr Lys Lys
                 325                 330                 335

Asp Ile Lys Ala Ala Val Arg Asn Met Ser Tyr Met Glu Lys Gly Thr
                 340                 345                 350

Met Thr Gly Ala Ala Leu Lys Tyr Leu Ile Asp Asn Ser Phe Thr Val
             355                 360                 365

Ser Ser Gly Ala Arg Pro Gly Ala Gln Lys Val Gly Ile Val Phe Thr
 370                 375                 380

Asp Gly Arg Ser Gln Asp Tyr Ile Asn Asp Ala Ala Lys Lys Ala Lys
385                 390                 395                 400

Asp Leu Gly Phe Lys Met Phe Ala Val Gly Val Gly Asn Ala Val Glu
                 405                 410                 415

Asp Glu Leu Arg Glu Ile Ala Ser Glu Pro Val Ala Glu His Tyr Phe
```

-continued

```
                420                      425                      430
Tyr Thr Ala Asp Phe Lys Thr Ile Asn Gln Ile Gly Lys Lys Leu Gln
        435                      440                 445

Lys Lys Ile Cys Val Glu Glu Asp Pro Cys Ala Cys Glu Ser Leu Val
    450                      455                 460

Lys Phe Gln Ala Lys Val Glu Gly Leu Leu Gln Ala Leu Thr Arg Lys
465                      470              475                  480

Leu Glu Ala Val Ser Lys Arg Leu Ala Ile Leu Glu Asn Thr Val Val
                485                  490                  495
```